(12) United States Patent
Hlavinka

(10) Patent No.: US 9,394,387 B2
(45) Date of Patent: Jul. 19, 2016

(54) SYNTHESIS OF ARYL COUPLED BIS PHENOXIDES AND THEIR USE IN OLEFIN POLYMERIZATION CATALYST SYSTEMS WITH ACTIVATOR-SUPPORTS

(71) Applicant: Chevron Phillips Chemical Company LP, The Woodlands, TX (US)

(72) Inventor: Mark L. Hlavinka, Tulsa, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/277,915

(22) Filed: May 15, 2014

(65) Prior Publication Data

US 2015/0329652 A1  Nov. 19, 2015

(51) Int. Cl.
| | | |
|---|---|---|
| C07F 7/00 | (2006.01) | |
| C08F 110/02 | (2006.01) | |
| C07D 213/127 | (2006.01) | |
| C07D 213/30 | (2006.01) | |
| C08F 210/16 | (2006.01) | |
| C08F 4/64 | (2006.01) | |

(52) U.S. Cl.
CPC .......... *C08F 110/02* (2013.01); *C07D 213/127* (2013.01); *C07D 213/30* (2013.01); *C07F 7/00* (2013.01); *C07F 7/006* (2013.01); *C08F 210/16* (2013.01); *B01J 2531/48* (2013.01); *C08F 4/64158* (2013.01)

(58) Field of Classification Search
CPC ................................ C07F 7/00; C08F 4/64158
See application file for complete search history.

(56) References Cited

U.S. PATENT DOCUMENTS

| | | | |
|---|---|---|---|
| 3,242,099 A | 3/1966 | Manyik | |
| 3,248,179 A | 4/1966 | Norwood | |
| 4,501,885 A | 2/1985 | Sherk et al. | |
| 4,588,790 A | 5/1986 | Jenkins, III et al. | |
| 4,794,096 A | 12/1988 | Ewen | |
| 4,808,561 A | 2/1989 | Welborn | |
| 5,352,749 A | 10/1994 | DeChellis et al. | |
| 5,436,304 A | 7/1995 | Griffin et al. | |
| 5,455,314 A | 10/1995 | Burns et al. | |
| 5,565,175 A | 10/1996 | Hottovy et al. | |
| 5,575,979 A | 11/1996 | Hanson | |
| 5,576,259 A | 11/1996 | Hasegawa | |
| 5,739,220 A | 4/1998 | Shamshoum et al. | |
| 5,807,938 A | 9/1998 | Kaneko | |
| 5,919,983 A | 7/1999 | Rosen | |
| 6,107,230 A | 8/2000 | McDaniel et al. | |
| 6,165,929 A | 12/2000 | McDaniel et al. | |
| 6,239,235 B1 | 5/2001 | Hottovy et al. | |
| 6,262,191 B1 | 7/2001 | Hottovy et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 | 12/2003 | Hawley et al. | |
| 6,750,302 B1 | 6/2004 | McDaniel et al. | |
| 6,825,296 B2 * | 11/2004 | Chi-Wang Chan | C07F 7/006 502/155 |
| 7,250,510 B2 | 7/2007 | Organ et al. | |
| 7,294,599 B2 | 11/2007 | Jensen et al. | |
| 7,601,665 B2 | 10/2009 | McDaniel et al. | |
| 7,847,099 B2 * | 12/2010 | Agapie | C07F 7/00 502/103 |
| 7,858,784 B2 | 12/2010 | Buchwald et al. | |
| 7,884,163 B2 | 2/2011 | McDaniel et al. | |
| 8,114,946 B2 | 2/2012 | Yang et al. | |
| 8,153,544 B2 * | 4/2012 | Nagy | C08F 10/00 502/150 |
| 8,158,733 B2 * | 4/2012 | Nagy | C07F 7/00 502/103 |
| 8,309,485 B2 | 11/2012 | Yang et al. | |
| 8,436,133 B2 * | 5/2013 | Carpentier | C08G 63/823 502/150 |
| 8,519,070 B2 * | 8/2013 | Carpentier | C07F 7/00 502/113 |
| 8,618,229 B2 | 12/2013 | Hlavinka | |
| 8,623,973 B1 | 1/2014 | McDaniel et al. | |
| 8,703,886 B1 | 4/2014 | Yang et al. | |
| 2004/0059070 A1 | 3/2004 | Whitte et al. | |
| 2013/0137902 A1 | 5/2013 | Haddad et al. | |

FOREIGN PATENT DOCUMENTS

WO   2008/036882   3/2008

OTHER PUBLICATIONS

*Modern Plastics Encyclopedia*, Mid-Nov. 1995 Issue, vol. 72, No. 12, 3 pages.
*Film Extrusion Manual—Process, Materials, Properties*, TAPPI Press, 1992, 16 pages.
International Patent Application PCT/US2015/030529, dated Aug. 26, 2015.
Theodor Agapie, et al: "Zirconium and Titanium Complexes Supported by Tridentate LX2 Ligands Having Two Phenolates Linked to Furan, Thiophene, an Pyridine Donors: Precatalysts for Propylene Polymerization and Oligomerization," Organometallics, vol. 27, No. 23, 2008 pp. 6245-6256.
Golisz, S. R., et al: "Synthesis of Early Transition Metal Bisphenolate Complexes and Their Use as Olefin Polymerization Catalysts," Macromolecules, American Chemical Society, US, vol. 42, No. 22 (Nov. 24, 2009), pp. 8751-8762.

(Continued)

*Primary Examiner* — Rip A Lee
(74) *Attorney, Agent, or Firm* — Merchant & Gould P.C.

(57) ABSTRACT

Disclosed herein are methods of making bis(phenol) ligand compounds and transition metal bis(phenolate) compounds. The transition metal bis(phenolate) compounds can be used as components in catalyst systems for the polymerization of olefins.

26 Claims, 2 Drawing Sheets

(56) References Cited

OTHER PUBLICATIONS

Chan Michael C W. et al: "Synthesis, Structures, and Olefin Polymerization Characteristics of Group 4 Catalyst [Zr{(OAr)2py]C12(D)] (D=0-donors, C1 [HPR 3]) Supported by Tridentate Pyridine-2,6-bis(aryloxide) Ligands," Organometallics, ACS, Washington, DC, US, vol. 25, No. 3, (Jan. 30, 2006) pp. 785-792.

Chan Michael C W et al: "Surprising Activity for Group 4Polyolefin Catalysts [M{ (OAr)2 py} CL2(thf)] (M=Zr, Ti) Bearing Tridentate Pyridine-2,6-bis (aryloxide) Ligands," Journal of the Chemical Society, Dalton Transactions, Chemical Society. Letchworth, GB, No. 16, (Aug. 21, 2002), pp. 3085-3087.

* cited by examiner

SYNTHESIS OF ARYL COUPLED BIS PHENOXIDES AND THEIR USE IN OLEFIN POLYMERIZATION CATALYST SYSTEMS WITH ACTIVATOR-SUPPORTS

BACKGROUND OF THE INVENTION

The present invention relates generally to the synthesis of bis(phenol) ligand compounds and transition metal bis(phenolate) compounds. These transition metal bis(phenolate) compounds can be used as components in a catalyst system suitable for the polymerization of olefins.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Generally, the present invention is directed to methods for synthesizing transition metal bis(phenolate) compounds, catalyst compositions containing these bis(phenolate) compounds, methods for preparing catalyst compositions, methods for using the catalyst compositions to polymerize olefins, the polymer resins produced using such catalyst compositions, and articles produced using these polymer resins.

Disclosed herein are methods of making bis(phenol) ligand compounds having the following formula:

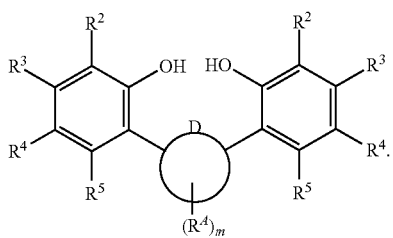

(II)

One such method can comprise (i) contacting a phenol compound having the formula:

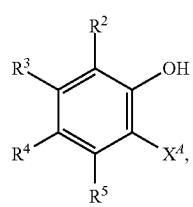

(III)

with (a) zinc metal, (b) a zinc-containing transfer agent, or (c) a halogen transfer agent and a zinc transfer compound; in the presence of a reaction solvent to form a first mixture; and (ii) contacting the first mixture with a palladium cross-coupling catalyst system and a substituted or unsubstituted, saturated or unsaturated, $C_4$ to $C_8$ heterocyclic compound having the formula:

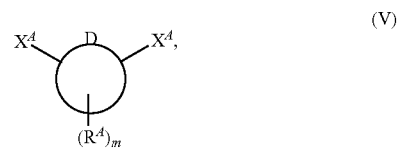

(V)

to form a ligand reaction mixture comprising the bis(phenol) ligand compound having formula (II).

Also disclosed herein are methods of making transition metal bis(phenolate) compounds having the following formula:

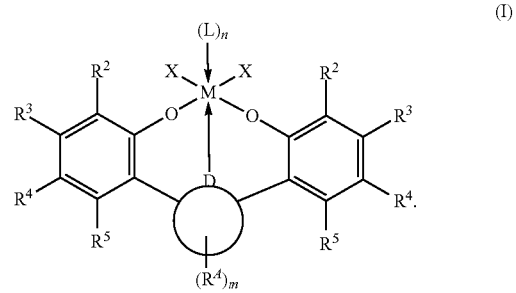

(I)

One such method can comprise (i) contacting a phenol compound having formula (III) with (a) zinc metal, (b) a zinc-containing transfer agent, or (c) a halogen transfer agent and a zinc transfer compound; in the presence of a reaction solvent to form a first mixture;

(ii) contacting the first mixture with a palladium cross-coupling catalyst system and a substituted or unsubstituted, saturated or unsaturated, $C_4$ to $C_8$ heterocyclic compound having formula (V), to form a ligand reaction mixture comprising a bis(phenol) ligand compound having formula (II); and (iii) contacting the ligand compound having formula (II) with M(X)(X)(X)(X), optionally in the presence of a second solvent, to form a transition metal compound reaction mixture comprising the transition metal bis(phenolate) compound having formula (I).

In these methods of synthesis, $R^2$, $R^3$, $R^4$, and $R^5$ independently can be H or a $C_1$ to $C_{18}$ hydrocarbyl or halogenated hydrocarbyl group;

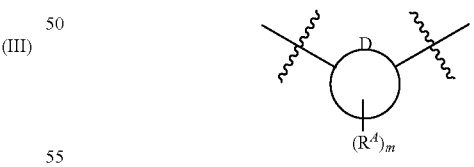

can be a substituted or unsubstituted, saturated or unsaturated, $C_4$ to $C_8$ heterocyclic group, wherein each $R^A$ independently can be a $C_1$ to $C_{18}$ hydrocarbyl or halogenated hydrocarbyl group, and m can be 0, 1, 2, or 3;

each $X^A$ independently can be Cl, Br, or I;

M can be Ti, Zr, or Hf;

each X independently can be a monoanionic ligand; and each L independently can be a neutral ligand, wherein n can be 0, 1 or 2.

Other aspects of the present invention are directed to catalyst compositions containing any transition metal bis(phenolate) compound having formula (I) disclosed herein, any activator-support disclosed herein, and optionally, any co-catalyst disclosed herein. Such catalyst compositions can be used to produce, for example, ethylene-based homopolymers and copolymers for variety of end-use applications.

The present invention also contemplates and encompasses olefin polymerization processes. Such processes can comprise contacting a catalyst composition with an olefin monomer and optionally an olefin comonomer under polymerization conditions to produce an olefin polymer. Generally, the catalyst composition employed can comprise any of the transition metal bis(phenolate) compounds and any of the activator-supports and optional co-catalysts disclosed herein. For example, organoaluminum compounds can be utilized in the catalyst compositions and/or polymerization processes.

Polymers produced from the polymerization of olefins, resulting in homopolymers, copolymers, terpolymers, etc., can be used to produce various articles of manufacture. A representative and non-limiting example of an olefin polymer (e.g., an ethylene homopolymer or copolymer) consistent with aspects of this invention can be characterized by the following properties: a ratio of Mw/Mn in a range from about 1.5 to about 5, and a Mw in a range from about 1,500,000 to about 5,000,000 g/mol. Another representative and non-limiting ethylene-based polymer described herein can have a ratio of Mw/Mn in a range from about 10 to about 200, and a Mw in a range from about 100,000 to about 800,000 g/mol.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects and embodiments may be directed to various feature combinations and sub-combinations described in the detailed description.

DEFINITIONS

Figure 1:
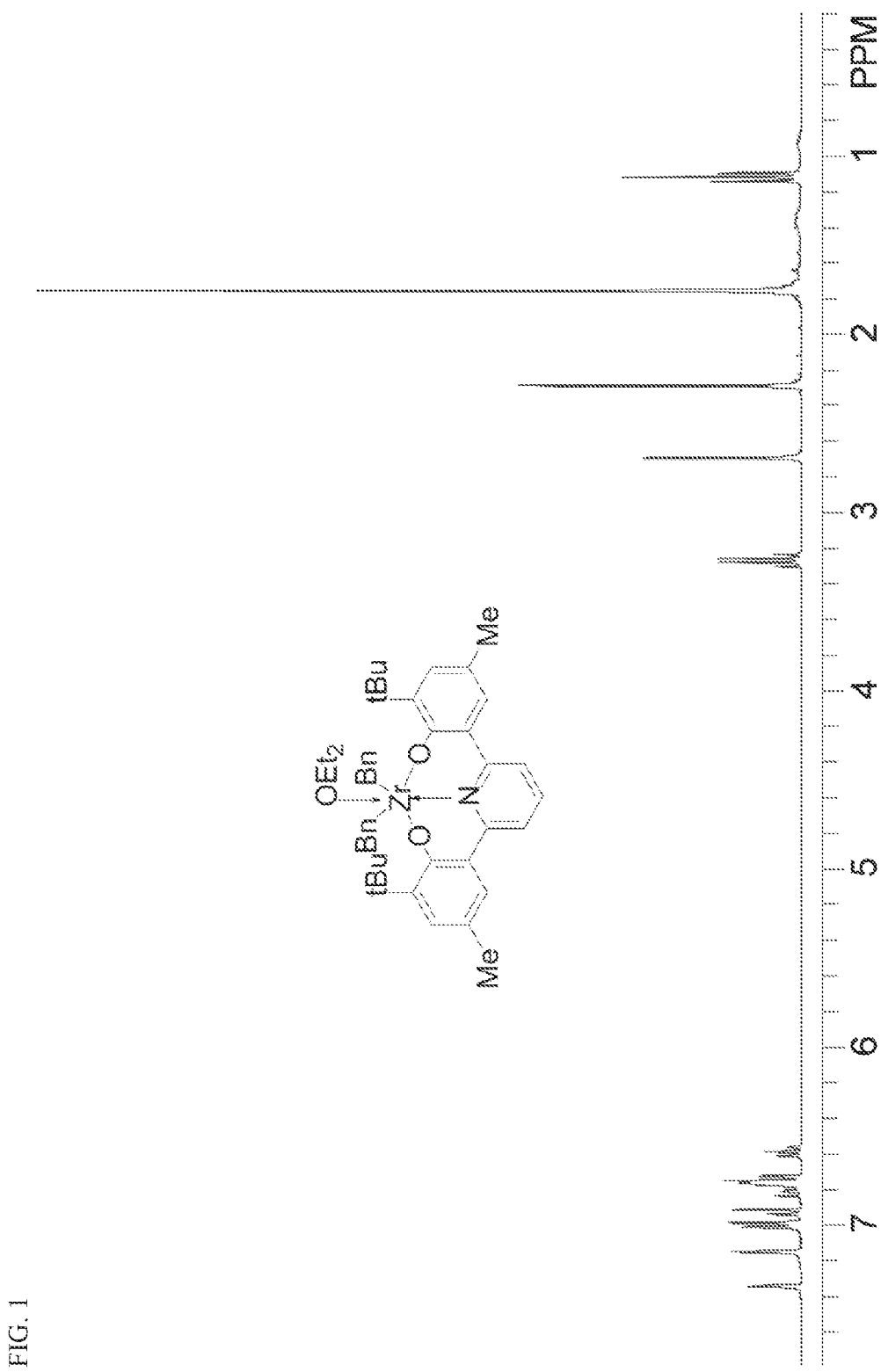
FIG. 1 presents a $^1$H-NMR plot of the zirconium bis(phenolate) compound of Example 2.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described herein in terms of "comprising" various components or steps, the compositions and methods can also "consist essentially of" or "consist of" the various components or steps, unless stated otherwise. For example, a catalyst composition consistent with aspects of the present invention can comprise; alternatively, can consist essentially of; or alternatively, can consist of;

(i) a transition metal bis(phenolate) compound, (ii) an activator-support, and (iii) optionally, a co-catalyst.

The terms "a," "an," "the," etc., are intended to include plural alternatives, e.g., at least one, unless otherwise specified. For instance, the disclosure of "an activator-support" or "a bis(phenolate) compound" is meant to encompass one, or mixtures or combinations of more than one, activator-support or bis(phenolate) compound, respectively, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane, while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. Unless otherwise specified, "substituted" is intended to be non-limiting and include inorganic substituents or organic substituents as understood by one of ordinary skill in the art.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Non-limiting examples of hydrocarbyl groups include alkyl, alkenyl, aryl, and aralkyl groups, amongst other groups.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer can be categorized an as ethylene/1-hexene copolymer.

In like manner, the scope of the term "polymerization" includes homopolymerization, copolymerization, terpolymerization, etc. Therefore, a copolymerization process can involve contacting one olefin monomer (e.g., ethylene) and one olefin comonomer (e.g., 1-hexene) to produce a copolymer.

The term "co-catalyst" is used generally herein to refer to compounds such as aluminoxane compounds, organoboron or organoborate compounds, ionizing ionic compounds, organoaluminum compounds, organozinc compounds, organomagnesium compounds, organolithium compounds, and the like, that can constitute one component of a catalyst composition, when used, for example, in addition to an activator-support. The term "co-catalyst" is used regardless of the actual function of the compound or any chemical mechanism by which the compound may operate.

The terms "chemically-treated solid oxide," "treated solid oxide compound," and the like, are used herein to indicate a solid, inorganic oxide of relatively high porosity, which can exhibit Lewis acidic or Brønsted acidic behavior, and which has been treated with an electron-withdrawing component, typically an anion, and which is calcined. The electron-withdrawing component is typically an electron-withdrawing anion source compound. Thus, the chemically-treated solid oxide can comprise a calcined contact product of at least one solid oxide with at least one electron-withdrawing anion source compound. Typically, the chemically-treated solid oxide comprises at least one acidic solid oxide compound. The "activator-support" of the present invention can be a chemically-treated solid oxide. The terms "support" and "activator-support" are not used to imply these components are inert, and such components should not be construed as an inert component of the catalyst composition. The term "activator," as used herein, refers generally to a substance that is capable of converting a transition metal component into a catalyst that can polymerize olefins, or converting a contact product of a transition metal component and a component that provides an activatable ligand (e.g., an alkyl, a hydride) to the transition metal component, when the transition metal compound does not already comprise such a ligand, into a catalyst that can polymerize olefins. This term is used regardless of the actual activating mechanism. Illustrative activators include activator-supports, aluminoxanes, organoboron or organoborate compounds, ionizing ionic compounds, and the like. Aluminoxanes, organoboron or organoborate compounds, and ionizing ionic compounds generally are referred to as activators if used in a catalyst composition in which an activator-support is not present. If the catalyst composition contains an activator-support, then the aluminoxane, organoboron or organoborate, and ionizing ionic materials are typically referred to as co-catalysts.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the co-catalyst, the transition metal compound(s), or the activator (e.g., activator-support), after combining these components. Therefore, the terms "catalyst composition," "catalyst mixture," "catalyst system," and the like, encompass the initial starting components of the composition, as well as whatever product(s) may result from contacting these initial starting components, and this is inclusive of both heterogeneous and homogenous catalyst systems or compositions. The terms "catalyst composition," "catalyst mixture," "catalyst system," and the like, can be used interchangeably throughout this disclosure.

The term "contact product" is used herein to describe compositions wherein the components are contacted together in any order, in any manner, and for any length of time. For example, the components can be contacted by blending or mixing. Further, contacting of any component can occur in the presence or absence of any other component. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which can be blended, mixed, slurried, dissolved, reacted, treated, or otherwise contacted in some other manner. Therefore, the term "contacting" encompasses the "reacting" of two or more components, and it also encompasses the "mixing" or "blending" of two or more components that do not react with one another.

The term "in the presence of" a particular solvent is used herein to indicate that the components that are contacted or reacted in steps of a synthesis can occur "in" the solvent (e.g., in solution), but this is not a requirement. For instance, one or more of the components can be dissolved in the solvent. Additionally or alternatively, one or more of the components can be partially or completely insoluble in the solvent. Thus, the use of "in the presence of" a particular solvent is meant to include both single phase and multi-phase reaction systems. In many cases, one component can be dissolved in a solvent when contacted or reacted with one or more other components.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ hydrocarbyl group, or in alternative language, a hydrocarbyl group having from 1 to 18 carbon atoms, as used herein, refers to a moiety that can have 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the ratio of Mw/Mn of an olefin polymer produced in an aspect of this invention. By a disclosure that the Mw/Mn can be in a range from about 70 to about 150, Applicants intend to recite that the Mw/Mn can be any ratio in the range and, for example, can be equal to about 70, about 80, about 90, about 100, about 110, about 120, about 130, about 140, or about 150. Additionally, the Mw/Mn can be within any range from about 70 to about 150 (for example, from about 75 to about 125), and this also includes any combination of ranges between about 70 and about 150 (for example, the Mw/Mn can be in a range from about 70 to about 90, or from about 115 to about 145). Likewise, all other ranges disclosed herein should be interpreted in a manner similar to these examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

DETAILED DESCRIPTION OF THE INVENTION

The present invention is directed generally to the synthesis of bis(phenol) ligand compounds and to the synthesis of transition metal bis(phenolate) compounds. The present invention also is directed generally to catalyst compositions containing transition metal bis(phenolate) compounds, to polymerization processes utilizing such catalyst compositions, and to the resulting olefin polymers produced from the polymerization processes.

Synthesis of a Transition Metal Bis(Phenolate) Compound

In accordance with the present invention, methods of making transition metal bis(phenolate) compounds having the formula:

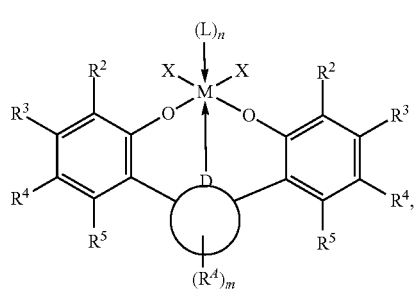

are disclosed.

In an aspect of this invention, a method of making a transition metal bis(phenolate) compound having formula (I) is provided and, in this aspect, the method can comprise:

(i) contacting a phenol compound having the formula:

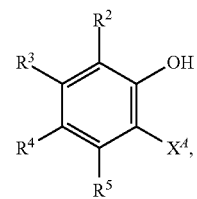

with
(a) zinc metal;
(b) a zinc-containing transfer agent; or
(c) a halogen transfer agent and a zinc transfer compound;
in the presence of a reaction solvent to form a first mixture;

(ii) contacting the first mixture with a palladium cross-coupling catalyst system and a substituted or unsubstituted, saturated or unsaturated, $C_4$ to $C_8$ heterocyclic compound having the formula:

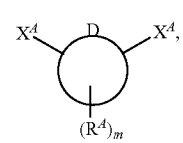

to form a ligand reaction mixture comprising a bis(phenol) ligand compound having formula (II):

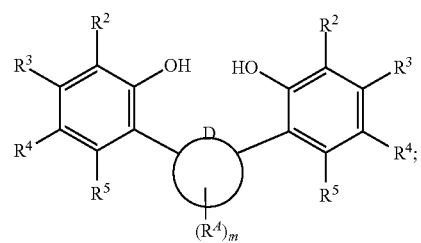

and
(iii) contacting the ligand compound having formula (II) with M(X)(X)(X)(X), optionally in the presence of a second solvent, to form a transition metal compound reaction mixture comprising the transition metal bis(phenolate) compound having formula (I).

In the method of making a transition metal bis(phenolate) compound having formula (I), $R^2$, $R^3$, $R^4$, and $R^5$ independently can be H or a $C_1$ to $C_{18}$ hydrocarbyl or halogenated hydrocarbyl group;

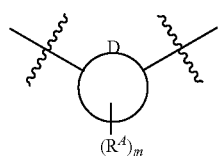

can be a substituted or unsubstituted, saturated or unsaturated, $C_4$ to $C_8$ heterocyclic group, wherein each $R^A$ independently can be a $C_1$ to $C_{18}$ hydrocarbyl or halogenated hydrocarbyl group, and m can be 0, 1, 2, or 3;

each $X^A$ independently can be Cl, Br, or I;

M can be Ti, Zr, or Hf;

each X independently can be a monoanionic ligand; and each L independently can be a neutral ligand, wherein n can be 0, 1 or 2.

Other methods for synthesizing compounds having formula (I) and formula (II) exist, however, these methods have notable shortcomings One such method requires a demethylation step with molten pyridinium chloride, making the synthesis commercially impractical. Another such method requires the use of a protecting group—e.g., methyl chloromethyl ether (MOMCl)—which has toxicity and disposal concerns, and requires the use of tert-butyllithium, which is pyrophoric and necessitates a reaction step at −108° C. The synthesis methods disclosed herein overcome these deficiencies (e.g., molten pyridinium chloride, use of a protecting group, required use of t-butyllithium, etc.).

Unless otherwise specified, formulas (I), (II), (III), and (V) above, any other structural formulas disclosed herein, and any species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In accordance with aspects of this invention, the metal (M) in formula (I) and in M(X)(X)(X)(X) can be Ti, Zr, or Hf. In one aspect, for instance, M can be Zr or Hf, while in another aspect, M can be Ti; alternatively, M can be Zr; or alternatively, M can be Hf.

Each X in formula (I) and in M(X)(X)(X)(X) in the processes described herein independently can be a monoanionic ligand. In some aspects, suitable monoanionic ligands can include, but are not limited to, H (hydride), $BH_4$, a halide, a $C_1$ to $C_{36}$ hydrocarbyl group, a $C_1$ to $C_{36}$ hydrocarboxy group, a $C_1$ to $C_{36}$ hydrocarbylaminyl group, a $C_1$ to $C_{36}$ hydrocarbylsilyl group, a $C_1$ to $C_{36}$ hydrocarbylaminylsilyl group, —$OBR^1_2$, or —$OSO_2R^1$, wherein $R^1$ is a $C_1$ to $C_{36}$ hydrocarbyl group. It is contemplated that each X can be either the same or a different monoanionic ligand. As one of skill in the art would readily recognize, the two independent monoanionic ligands in formula (I) can be the same as at least two of the monoanionic ligands in M(X)(X)(X)(X).

In one aspect, each X independently can be H, $BH_4$, a halide (e.g., F, Cl, Br, etc.), a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, or a $C_1$ to $C_{18}$ hydrocarbylaminylsilyl group. Alternatively, each X independently can be H, $BH_4$, a halide, $OBR^1_2$, or $OSO_2R^1$, wherein $R^1$ is a $C_1$ to $C_{18}$ hydrocarbyl group. In another aspect, each X independently can be H, $BH_4$, a halide, a $C_1$ to $C_{12}$ hydrocarbyl group, a $C_1$ to $C_{12}$ hydrocarboxy group, a $C_1$ to $C_{12}$ hydrocarbylaminyl group, a $C_1$ to $C_{12}$ hydrocarbylsilyl group, a $C_1$ to $C_{12}$ hydrocarbylaminylsilyl group, $OBR^1_2$, or $OSO_2R^1$, wherein $R^1$ is a $C_1$ to $C_{12}$ hydrocarbyl group. In another aspect, each X independently can be H, $BH_4$, a halide, a $C_1$ to $C_{10}$ hydrocarbyl group, a $C_1$ to $C_{10}$ hydrocarboxy group, a $C_1$ to $C_{10}$ hydrocarbylaminyl group, a $C_1$ to $C_{10}$ hydrocarbylsilyl group, a $C_1$ to $C_{10}$ hydrocarbylaminylsilyl group, $OBR^1_2$, or $OSO_2R^1$, wherein $R^1$ is a $C_1$ to $C_{10}$ hydrocarbyl group. In yet another aspect, each X independently can be H, $BH_4$, a halide, a $C_1$ to $C_8$ hydrocarbyl group, a $C_1$ to $C_8$ hydrocarboxy group, a $C_1$ to $C_8$ hydrocarbylaminyl group, a $C_1$ to $C_8$ hydrocarbylsilyl group, a $C_1$ to $C_8$ hydrocarbylaminylsilyl group, $OBR^1_2$, or $OSO_2R^1$, wherein $R^1$ is a $C_1$ to $C_8$ hydrocarbyl group. In still another aspect, each X independently can be a halide or a $C_1$ to $C_{18}$ hydrocarbyl group. For example, each X can be Cl.

The hydrocarbyl group which can be an X in formula (I) and M(X)(X)(X)(X) can be a $C_1$ to $C_{36}$ hydrocarbyl group, including, but not limited to, a $C_1$ to $C_{36}$ alkyl group, a $C_2$ to $C_{36}$ alkenyl group, a $C_4$ to $C_{36}$ cycloalkyl group, a $C_6$ to $C_{36}$ aryl group, or a $C_7$ to $C_{36}$ aralkyl group. For instance, each X independently can be a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, each X independently can be a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; alternatively, each X independently can be a $C_1$ to $C_{10}$ alkyl group, a $C_2$ to $C_{10}$ alkenyl group, a $C_4$ to $C_{10}$ cycloalkyl group, a $C_6$ to $C_{10}$ aryl group, or a $C_7$ to $C_{10}$ aralkyl group; or alternatively, each X independently can be a $C_1$ to $C_5$ alkyl group, a $C_2$ to $C_5$ alkenyl group, a $C_5$ to $C_8$ cycloalkyl group, a $C_6$ to $C_8$ aryl group, or a $C_7$ to $C_8$ aralkyl group.

Accordingly, in some aspects, the alkyl group which can be an X can be a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, or an octadecyl group; or alternatively, a methyl group, an ethyl group, a propyl group, a butyl group, a pentyl group, a hexyl group, a heptyl group, an octyl group, a nonyl group, or a decyl group. In some aspects, the alkyl group which can be an X can be a methyl group, an ethyl group, a n-propyl group, an iso-propyl group, a n-butyl group, an iso-butyl group, a sec-butyl group, a tert-butyl group, a n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group.

Suitable alkenyl groups which can be an X can include, but are not limited to, an ethenyl group, a propenyl group, a butenyl group, a pentenyl group, a hexenyl group, a heptenyl group, an octenyl group, a nonenyl group, a decenyl group, a undecenyl group, a dodecenyl group, a tridecenyl group, a tetradecenyl group, a pentadecenyl group, a hexadecenyl group, a heptadecenyl group, or an octadecenyl group. Such alkenyl groups can be linear or branched, and the double bond can be located anywhere in the chain. In one aspect, each X independently can be an ethenyl group, a propenyl group, a butenyl group, a pentenyl group, a hexenyl group, a heptenyl group, an octenyl group, a nonenyl group, or a decenyl group, while in another aspect, each X independently can be an ethenyl group, a propenyl group, a butenyl group, a pentenyl group, or a hexenyl group. For example, an X can be an ethenyl group; alternatively, a propenyl group; alternatively, a butenyl group; alternatively, a pentenyl group; or alternatively, a hexenyl group. In yet another aspect, an X can be a terminal alkenyl group, such as a $C_3$ to $C_{18}$ terminal alkenyl group, a $C_3$ to $C_{12}$ terminal alkenyl group, or a $C_3$ to $C_8$ terminal alkenyl group. Illustrative terminal alkenyl groups can include, but are not limited to, a prop-2-en-1-yl group, a bute-3-en-1-yl group, a pent-4-en-1-yl group, a hex-5-en-1-yl group, a hept-6-en-1-yl group, an octe-7-en-1-yl group, a non-8-en-1-yl group, a dece-9-en-1-yl group, and so forth.

Each X independently can be a cycloalkyl group, including, but not limited to, a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. For example, an X can be a cyclopentyl group, a substituted cyclopentyl group, a cyclohexyl group, or a substituted cyclohexyl group. Moreover, each X independently can be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; alternatively, a cyclooctyl group or a substituted cyclooctyl group; alternatively, a cyclopentyl group; alternatively, a substituted cyclopentyl group; alternatively, a cyclohexyl group; or alternatively, a substituted cyclohexyl group. Substituents which can be utilized for the substituted cycloalkyl group are independently disclosed herein and can be utilized without limitation to further describe the substituted cycloalkyl group which can be an X.

In some aspects, the aryl group which can be an X can be a phenyl group, a substituted phenyl group, a naphthyl group, or a substituted naphthyl group. In an aspect, the aryl group can be a phenyl group or a substituted phenyl group; alternatively, a naphthyl group or a substituted naphthyl group; alternatively, a phenyl group or a naphthyl group; alternatively, a substituted phenyl group or a substituted naphthyl group; alternatively, a phenyl group; or alternatively, a naphthyl group. Substituents which can be utilized for the substituted phenyl groups or substituted naphthyl groups are independently disclosed herein and can be utilized without limitation to further describe the substituted phenyl groups or substituted naphthyl groups which can be an X in formula (I) and M(X)(X)(X)(X).

In an aspect, the substituted phenyl group which can be an X can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other aspects, the substituted phenyl group can be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents which can be utilized for these specific substituted phenyl groups are independently disclosed herein and can be utilized without limitation to further describe these substituted phenyl groups which can be an X group(s) in formula (I) and M(X)(X)(X)(X).

In some aspects, the aralkyl group which can be an X group can be a benzyl group or a substituted benzyl group. In an aspect, the aralkyl group can be a benzyl group or, alternatively, a substituted benzyl group. Substituents which can be utilized for the substituted aralkyl group are independently disclosed herein and can be utilized without limitation to further describe the substituted aralkyl group which can be an X group(s).

In an aspect, each non-hydrogen substituent(s) for the substituted cycloalkyl group, substituted aryl group, or substituted aralkyl group which can be an X in formula (I) and M(X)(X)(X)(X) independently can be a $C_1$ to $C_{18}$ hydrocarbyl group; alternatively, a $C_1$ to $C_8$ hydrocarbyl group; or alternatively, a $C_1$ to $C_5$ hydrocarbyl group. Specific hydrocarbyl groups are independently disclosed herein and can be utilized without limitation to further describe the substituents of the substituted cycloalkyl groups, substituted aryl groups, or substituted aralkyl groups which can be an X. For instance, the hydrocarbyl substituent can be an alkyl group, such as a methyl group, an ethyl group, a n-propyl group, an isopropyl group, a n-butyl group, a sec-butyl group, an isobutyl group, a tert-butyl group, a n-pentyl group, a 2-pentyl group, a 3-pentyl group, a 2-methyl-1-butyl group, a tert-pentyl group, a 3-methyl-1-butyl group, a 3-methyl-2-butyl group, or a neopentyl group, and the like. Furthermore, the hydrocarbyl substituent can be a benzyl group, a phenyl group, a tolyl group, or a xylyl group, and the like.

A hydrocarboxy group is used generically herein to include, for instance, alkoxy, aryloxy, aralkoxy, -(alkyl, aryl, or aralkyl)-O-(alkyl, aryl, or aralkyl) groups, and —O(CO)-(hydrogen or hydrocarbyl) groups, and these groups can comprise up to about 36 carbon atoms (e.g., $C_1$ to $C_{36}$, $C_1$ to $C_{18}$, $C_1$ to $C_{10}$, or $C_1$ to $C_8$ hydrocarboxy groups). Illustrative and non-limiting examples of hydrocarboxy groups which can be an X in formula (I) and M(X)(X)(X)(X) can include, but are not limited to, a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, a neo-pentoxy group, a phenoxy group, a toloxy group, a xyloxy group, a 2,4,6-trimethylphenoxy group, a benzoxy group, an acetylacetonate group (acac), a formate group, an acetate group, a stearate group, an oleate group, a benzoate group, and the like. In an aspect, the hydrocarboxy group which can be an X can be a methoxy group; alternatively, an ethoxy group; alternatively, an n-propoxy group; alternatively, an isopropoxy group; alternatively, an n-butoxy group; alternatively, a sec-butoxy group; alternatively, an isobutoxy group; alternatively, a tert-butoxy group; alternatively, an n-pentoxy group; alternatively, a 2-pentoxy group; alternatively, a 3-pentoxy group; alternatively, a 2-methyl-1-butoxy group; alternatively, a tert-pentoxy group; alternatively, a 3-methyl-1-butoxy group, alternatively, a 3-methyl-2-butoxy group; alternatively, a neo-pentoxy group; alternatively, a phenoxy group; alternatively, a toloxy group; alternatively, a xyloxy group; alternatively, a 2,4,6-trimethylphenoxy group; alternatively, a benzoxy group; alternatively, an acetylacetonate group; alternatively, a formate group; alternatively, an acetate group; alternatively, a stearate group; alternatively, an oleate group; or alternatively, a benzoate group.

The term hydrocarbylaminyl group is used generically herein to refer collectively to, for instance, alkylaminyl, arylaminyl, aralkylaminyl, dialkylaminyl, diarylaminyl, diaralkylaminyl, and -(alkyl, aryl, or aralkyl)-N-(alkyl, aryl, or aralkyl) groups, and unless otherwise specified, the hydrocarbylaminyl groups which can be an X in formula (I) and M(X)(X)(X)(X) can comprise up to about 36 carbon atoms (e.g., $C_1$ to $C_{36}$, $C_1$ to $C_{18}$, $C_1$ to $C_{10}$, or $C_1$ to $C_8$ hydrocarbylaminyl groups). Accordingly, hydrocarbylaminyl is intended to cover both (mono)hydrocarbylaminyl and dihydrocarbylaminyl groups. In some aspects, the hydrocarbylaminyl group which can be an X can be, for instance, a methylaminyl group (—NHCH$_3$), an ethylaminyl group (—NHCH$_2$CH$_3$), an n-propylaminyl group (—NHCH$_2$CH$_2$CH$_3$), an iso-propylaminyl group (—NHCH(CH$_3$)$_2$), an n-butylaminyl group (—NHCH$_2$CH$_2$CH$_2$CH$_3$), a t-butylaminyl group (—NHC(CH$_3$)$_3$), an n-pentylaminyl group (—NHCH$_2$CH$_2$CH$_2$CH$_2$CH$_3$), a neo-pentylaminyl group (—NHCH$_2$C(CH$_3$)$_3$), a phenylaminyl group (—NHC$_6$H$_5$), a tolylaminyl group (—NHC$_6$H$_4$CH$_3$), or a xylylaminyl group (—NHC$_6$H$_3$(CH$_3$)$_2$); alternatively, a methylaminyl group; alternatively, an ethylaminyl group; alternatively, a propylaminyl group; or alternatively, a phenylaminyl group. In other aspects, the hydrocarbylaminyl group which can be an X can be, for instance, a dimethylaminyl group (—N(CH$_3$)$_2$), a diethylaminyl group (—N(CH$_2$CH$_3$)$_2$), a di-n-propylaminyl group (—N(CH$_2$CH$_2$CH$_3$)$_2$), a di-iso-propylaminyl group (—N(CH(CH$_3$)$_2$)$_2$), a di-n-butylaminyl group (—N(CH$_2$CH$_2$CH$_2$CH$_3$)$_2$), a di-t-butylaminyl group (—N(C(CH$_3$)$_3$)$_2$), a di-n-pentylaminyl group (—N(CH$_2$CH$_2$CH$_2$CH$_2$CH$_3$)$_2$), a di-neo-pentylaminyl group (—N(CH$_2$C(CH$_3$)$_3$)$_2$), a di-phenylaminyl group (—N(C$_6$H$_5$)$_2$), a di-tolylaminyl group (—N(C$_6$H$_4$CH$_3$)$_2$), or a di-xylylaminyl group (—N(C$_6$H$_3$(CH$_3$)$_2$)$_2$); alternatively, a dimethylaminyl group; alternatively, a di-ethylaminyl group; alternatively, a di-n-propylaminyl group; or alternatively, a di-phenylaminyl group.

In accordance with some aspects disclosed herein, each X independently can be a $C_1$ to $C_{36}$ hydrocarbylsilyl group; alternatively, a $C_1$ to $C_{24}$ hydrocarbylsilyl group; alternatively, a $C_1$ to $C_{18}$ hydrocarbylsilyl group; or alternatively, a $C_1$ to $C_8$ hydrocarbylsilyl group. In an aspect, each hydrocarbyl (one or more) of the hydrocarbylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_2$ to $C_8$ aralkyl group, etc.). As used herein, hydrocarbylsilyl is intended to cover (mono)hydrocarbylsilyl (—SiH$_2$R), dihydrocarbylsilyl (—SiHR$_2$), and trihydrocarbylsilyl (—SiR$_3$) groups, with R being a hydrocarbyl group. In one aspect, the hydrocarbylsilyl group can be a $C_3$ to $C_{36}$ or a $C_3$ to $C_{18}$ trihydrocarbylsilyl group, such as, for example, a trialkylsilyl group or a triphenylsilyl group. Illustrative and non-limiting examples of hydrocarbylsilyl groups which can be an X group(s) can include, but are not limited to, trimethylsilyl, triethylsilyl, tripropylsilyl (e.g., triisopropylsilyl), tributylsilyl, tripentylsilyl, triphenylsilyl, allyldimethylsilyl, and the like.

A hydrocarbylaminylsilyl group is used herein to refer to groups containing at least one hydrocarbon moiety, at least one N atom, and at least one Si atom. Illustrative and non-limiting examples of hydrocarbylaminylsilyl groups which can be an X can include, but are not limited to —N(SiMe$_3$)$_2$, —N(SiEt$_3$)$_2$, and the like. Unless otherwise specified, the hydrocarbylaminylsilyl groups which can be X can comprise up to about 36 carbon atoms (e.g., $C_1$ to $C_{36}$, $C_1$ to $C_{18}$, $C_1$ to $C_{12}$, or $C_1$ to $C_8$ hydrocarbylaminylsilyl groups). In an aspect, each hydrocarbyl (one or more) of the hydrocarbylaminylsilyl group can be any hydrocarbyl group disclosed herein (e.g., a $C_1$ to $C_5$ alkyl group, a $C_2$ to $C_5$ alkenyl group, a $C_5$ to $C_8$ cycloalkyl group, a $C_6$ to $C_8$ aryl group, a $C_7$ to $C_8$ aralkyl group, etc.). Moreover, hydrocarbylaminylsilyl is intended to cover —NH(SiH$_2$R), —NH(SiHR$_2$), —NH(SiR$_3$), —N(SiH$_2$R)$_2$, —N(SiHR$_2$)$_2$, and —N(SiR$_3$)$_2$ groups, among others, with R being a hydrocarbyl group.

In an aspect, each X independently can be —OBR$^1$$_2$ or —OSO$_2$R$^1$, wherein R$^1$ is a $C_1$ to $C_{36}$ hydrocarbyl group, or alternatively, a $C_1$ to $C_{18}$ hydrocarbyl group. The hydrocarbyl group in OBR$^1$$_2$ and/or OSO$_2$R$^1$ independently can be any hydrocarbyl group disclosed herein, such as, for instance, a $C_1$ to $C_{18}$ alkyl group, a $C_2$ to $C_{18}$ alkenyl group, a $C_4$ to $C_{18}$ cycloalkyl group, a $C_6$ to $C_{18}$ aryl group, or a $C_7$ to $C_{18}$ aralkyl group; alternatively, a $C_1$ to $C_{12}$ alkyl group, a $C_2$ to $C_{12}$ alkenyl group, a $C_4$ to $C_{12}$ cycloalkyl group, a $C_6$ to $C_{12}$ aryl group, or a $C_7$ to $C_{12}$ aralkyl group; or alternatively, a $C_1$ to $C_8$ alkyl group, a $C_2$ to $C_8$ alkenyl group, a $C_5$ to $C_8$ cycloalkyl group, a $C_6$ to $C_8$ aryl group, or a $C_7$ to $C_8$ aralkyl group.

In one aspect, each X independently can be H, BH$_4$, a halide, or a $C_1$ to $C_{36}$ hydrocarbyl group, hydrocarboxy group, hydrocarbylaminyl group, hydrocarbylsilyl group, or hydrocarbylaminylsilyl group, while in another aspect, each X independently can be H, BH$_4$, or a $C_1$ to $C_{18}$ hydrocarboxy group, hydrocarbylaminyl group, hydrocarbylsilyl group, or hydrocarbylaminylsilyl group. In yet another aspect, each X independently can be a halide; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group. In still another aspect, each X can be H; alternatively, F; alternatively, Cl; alternatively, Br; alternatively, I; alternatively, BH$_4$; alternatively, a $C_1$ to $C_{18}$ hydrocarbyl group; alternatively, a $C_1$ to $C_{18}$ hydrocarboxy group; alternatively, a $C_1$ to $C_{18}$ hydrocarbylaminyl group; alternatively, a $C_1$ to $C_{18}$ hydrocarbylsilyl group; or alternatively, a $C_1$ to $C_{18}$ hydrocarbylaminylsilyl group.

Each X independently can be, in some aspects, H, a halide, methyl, phenyl, benzyl, an alkoxy, an aryloxy, acetylacetonate, formate, acetate, stearate, oleate, benzoate, an alkylaminyl, a dialkylaminyl, a trihydrocarbylsilyl, or a hydrocarbylaminylsilyl; alternatively, H, a halide, methyl, phenyl, or benzyl; alternatively, an alkoxy, an aryloxy, or acetylacetonate; alternatively, an alkylaminyl or a dialkylaminyl; alternatively, a trihydrocarbylsilyl or hydrocarbylaminylsilyl; alternatively, H or a halide; alternatively, methyl, phenyl, benzyl, an alkoxy, an aryloxy, acetylacetonate, an alkylaminyl, or a dialkylaminyl; alternatively, H; alternatively, a halide; alternatively, methyl; alternatively, phenyl; alternatively, benzyl; alternatively, an alkoxy; alternatively, an aryloxy; alternatively, acetylacetonate; alternatively, an alkylaminyl; alternatively, a dialkylaminyl; alternatively, a trihydrocarbylsilyl; or alternatively, a hydrocarbylaminylsilyl. In these and other aspects, the alkoxy, aryloxy, alkylaminyl, dialkylaminyl, trihydrocarbylsilyl, and hydrocarbylaminylsilyl can be a $C_1$ to $C_{36}$, a $C_1$ to $C_{18}$, a $C_1$ to $C_{12}$, or a $C_1$ to $C_8$ alkoxy, aryloxy, alkylaminyl, dialkylaminyl, trihydrocarbylsilyl, and hydrocarbylaminylsilyl.

Moreover, each X independently can be, in certain aspects, a halide or a $C_1$ to $C_{18}$ hydrocarbyl group; alternatively, a halide or a $C_1$ to $C_8$ hydrocarbyl group; alternatively, F, Cl, Br, I, methyl, benzyl, or phenyl; alternatively, Cl, methyl, benzyl, or phenyl; alternatively, Cl or benzyl; alternatively, a $C_1$ to $C_{18}$ alkoxy, aryloxy, alkylaminyl, dialkylaminyl, trihydrocarbylsilyl, or hydrocarbylaminylsilyl group; alternatively, a $C_1$ to $C_8$ alkoxy, aryloxy, alkylaminyl, dialkylaminyl, trihydrocarbylsilyl, or hydrocarbylaminylsilyl group; or alternatively, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, naphthyl, trimethylsilyl, triisopropylsilyl, triphenylsilyl, or allyldimethylsilyl.

In the methods disclosed herein, each $X^4$ independently can be Cl, Br, or I. In some aspects, each $X^4$ independently can be Br or I, while in other aspects, each $X^4$ can be Br.

In the methods disclosed herein, $R^2$, $R^3$, $R^4$, and $R^5$ independently can be H or a $C_1$ to $C_{18}$ hydrocarbyl or halogenated hydrocarbyl group. In one aspect, $R^2$, $R^3$, $R^4$, and $R^5$ independently can be H or a $C_1$ to $C_{12}$ hydrocarbyl or halogenated hydrocarbyl group; alternatively, H or a $C_1$ to $C_8$ hydrocarbyl or halogenated hydrocarbyl group; alternatively, H; alternatively, a $C_1$ to $C_{10}$ hydrocarbyl group; alternatively, a $C_1$ to $C_{12}$ halogenated hydrocarbyl group; alternatively, H or a $C_1$ to $C_8$ alkyl group; or alternatively, H or a $C_1$ to $C_6$ alkyl group. The $C_1$ to $C_{18}$ hydrocarbyl group (or alkyl group) can be any $C_1$ to $C_{18}$ hydrocarbyl group (or alkyl group) described herein (e.g., as pertaining to X in formula (I)). In another aspect, one or more of $R^2$, $R^3$, $R^4$, and $R^5$ independently can be a $C_1$ to $C_{18}$ halogenated hydrocarbyl group, where the halogenated hydrocarbyl group indicates the presence of one or more halogen atoms replacing an equivalent number of hydrogen atoms in the hydrocarbyl group. The halogenated hydrocarbyl group often can be a halogenated alkyl group, a halogenated alkenyl group, a halogenated cycloalkyl group, a halogenated aryl group, or a halogenated aralkyl group. Representative and non-limiting halogenated hydrocarbyl groups include pentafluorophenyl, trifluoromethyl ($CF_3$), and the like. Yet, in other aspects, $R^2$, $R^3$, $R^4$, and $R^5$ independently can be H or a $C_1$ to $C_6$ alkyl group, such as methyl, ethyl, propyl, butyl, etc. In still another aspect, $R^2$ and $R^4$ independently can be a $C_1$ to $C_6$ alkyl group, and $R^3$ and $R^5$ can be H.

In the methods disclosed herein,

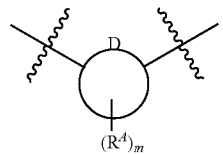

can be a substituted or unsubstituted, saturated or unsaturated, $C_4$ to $C_8$ heterocyclic group. Each $R^A$ independently can be a $C_1$ to $C_{18}$ hydrocarbyl or halogenated hydrocarbyl group, for instance, any $C_1$ to $C_{18}$ hydrocarbyl or halogenated hydrocarbyl group disclosed herein (see selections for $R^2$, $R^3$, $R^4$, and $R^5$), and m can be 0, 1, 2, or 3. In another aspect, the heterocyclic group can be a substituted or unsubstituted, saturated or unsaturated, $C_4$ to $C_5$ heterocyclic group, each $R^A$ independently can be any $C_1$ to $C_{18}$ hydrocarbyl or halogenated hydrocarbyl group disclosed herein, and m can be 0, 1, or 2; alternatively, m can be equal to 0; alternatively, m can be equal to 1; or alternatively, m can be equal to 2. In yet another aspect, the heterocyclic group can be:

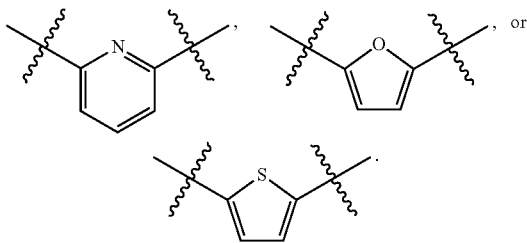

In the methods disclosed herein, each L in formula (I) independently can be a neutral ligand, and the integer n can be 0, 1 or 2. In an aspect, suitable neutral ligands can include sigma-donor solvents that contain a coordinating atom (or atoms) that can coordinate to a transition metal atom in formula (I). Examples of suitable coordinating atoms in the neutral ligands can include, but are not limited to, O, N, S, and P, or combinations of these atoms. Unless otherwise specified, the neutral ligand can be unsubstituted or can be substituted. Substituent groups are independently described herein and can be utilized, without limitation to further describe a neutral ligand which can be utilized as L in formula (I). In some aspects, the neutral ligand can be a Lewis base. When the integer n is equal to 2, it is contemplated that the two neutral ligands can be either the same or different. In other aspects, n can be equal to 0 or 1; alternatively, n can be equal to 0; or alternatively, n can be equal to 1.

In an aspect, each neutral ligand, L, independently can be an ether, an organic carbonyl, a thioether, an amine, a nitrile, or a phosphine. In another aspect, each neutral ligand independently can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers which can be utilized as a neutral ligand, either alone or in combination, can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls included ketones, aldehydes, esters, and amides which can be utilized as a neutral ligand, either alone or in combination, and illustrative examples can include, but are not limited to, acetone, acetophenone, benzophenone, N,N-dimethylformamide, N,N-dimethylacetamide, methyl acetate, ethyl acetate, and the like, including substituted derivatives thereof.

Suitable thioethers which can be utilized as a neutral ligand, either alone or in combination, can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles which can be utilized as a neutral ligand, either alone or in combination, can include, but are not limited to, acetonitrile, propionitrile, butyronitrile, benzonitrile, 4-methylbenzonitrile, and the like, including substituted derivatives thereof.

Suitable amines which can be utilized as a neutral ligand, either alone or in combination, can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, and the like, including substituted derivatives thereof. Suitable amines can be primary amines, secondary amines, or tertiary amines.

Suitable phosphines which can be utilized as a neutral ligand, either alone or in combination, can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, and the like, including substituted derivatives thereof.

In some aspects, each neutral ligand independently can be tetrahydrofuran, diethyl ether, acetonitrile, pyridine, dimethyl amine, diethyl amine, trimethyl amine, trimethylphosphine, or triphenylphosphine. In other aspects, each neutral ligand can be tetrahydrofuran; alternatively, diethyl ether; alternatively, acetonitrile; alternatively, pyridine; alternatively, dimethyl amine; alternatively, diethyl amine; alternatively, trimethyl amine; alternatively, trimethylphosphine; or alternatively, triphenylphosphine. Suitable neutral ligands are not limited to the neutral ligands described herein; other suitable neutral ligands are disclosed in U.S. Pat. No. 8,618,229, which is incorporated herein by reference in its entirety.

An illustrative and non-limiting example of a transition metal bis(phenolate) compound having formula (I) that can be produced using the methods described herein is the following compound (Me=methyl, $^t$Bu=tert-butyl, Bn=benzyl, Et=ethyl):

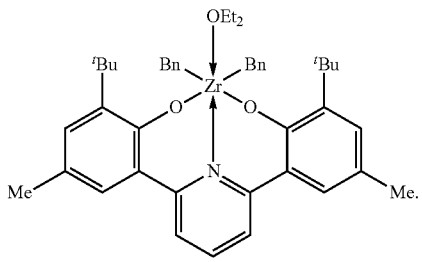

In accordance with one aspect of the method of making a bis(phenolate) compound having formula (I), the phenol compound having formula (III) can be contacted with zinc metal in the presence of a reaction solvent to form a first mixture. In further aspects, step (i) also can include an alkali metal salt and/or an alkaline earth metal salt. For instance, the phenol compound having formula (III) can be contacted with zinc metal and, optionally, any suitable alkali metal salt and/or alkaline earth metal salt. Illustrative and non-limiting examples of such salts can include LiCl, NaCl, KCl, NaBr, MgBr$_2$, MgCl$_2$, and the like, as well as combinations thereof. In these aspects, the zinc metal and the metal salt can be contacted with the phenol compound in any order, or simultaneously.

In accordance with another aspect of the method of making a bis(phenolate) compound having formula (I), the phenol compound having formula (III) can be contacted with a zinc-containing transfer agent in the presence of a reaction solvent to form a first mixture. The zinc-containing transfer agent can be any suitable zinc hydrocarbyl or zinc alkyl, for instance, where the hydrocarbyl or alkyl is any hydrocarbyl group or alkyl group disclosed herein (e.g., as pertaining to X in formula (I), $C_1$ to $C_{12}$ hydrocarbyl groups, $C_1$ to $C_8$ alkyl groups, etc.). Dimethyl zinc and diethyl zinc are representative and non-limiting examples of suitable zinc-containing transfer agents. In further aspects, step (i) also can include an alkali metal and/or an alkaline earth metal halogen or alkyl promoter. For instance, the phenol compound having formula (III) can be contacted with a zinc-containing transfer agent and any suitable alkali metal and/or alkaline earth metal halogen or alkyl promoter. Illustrative and non-limiting examples of such promoters can include LiCl, MeLi, NaCl, KCl, NaBr, MgBr$_2$, MgCl$_2$, and the like, as well as combinations thereof.

In these aspects, the zinc-containing transfer agent and the promoter can be contacted with the phenol compound in any order, or simultaneously.

In accordance with yet another aspect of the method of making a bis(phenolate) compound having formula (I), the phenol compound having formula (III) can be contacted with a halogen transfer agent and a zinc transfer compound in the presence of a reaction solvent to form a first mixture. In some aspects, the phenol compound can be contacted with the halogen transfer agent and the zinc transfer compound concurrently, while in other aspects, the phenol compound can be contacted with the halogen transfer agent prior to the zinc transfer compound. In one aspect, the halogen transfer agent can comprise a strong base, a strong Bronsted base, an alkali metal hydride or hydrocarbon compound, or an alkaline earth metal hydride or hydrocarbon compound, as well as mixtures or combinations thereof. In another aspect, the halogen transfer agent can comprise lithium, sodium, potassium, or magnesium metal; mixtures of these metals also can be used, if desired. In yet another aspect, the halogen transfer agent can comprise any suitable hydrocarbyl lithium, hydrocarbyl sodium, hydrocarbyl potassium, hydrocarbyl magnesium, alkyl lithium, alkyl sodium, alkyl potassium, alkyl magnesium, aryl lithium, aryl sodium, aryl potassium, or aryl magnesium compound, for instance, where the hydrocarbyl/alkyl/aryl are any hydrocarbyl/alkyl/aryl group disclosed herein (e.g., as pertaining to X in formula (I)). In still another aspect, the halogen transfer agent can comprise MeLi, n-BuLi, t-BuLi, n-hexylLi, LiCH$_2$SiMe$_3$, LiCH$_2$Ph, LiCH$_2$CMe$_3$, PrMgCl, PhMgCl, EtMgBr, mesitylmagnesium bromide, Bu$_3$MgLi, i-PrBu$_2$MgLi, and the like, as well as combinations thereof (Me=methyl, n-Bu=n-butyl, t-Bu=tert-butyl, Ph=phenyl, Pr=propyl, Et=ethyl, Bu=butyl, and i-Pr=isopropyl). For instance, n-BuLi can be used in particular aspects of this invention. Generally, the zinc transfer compound can comprise a compound having the formula: Zn(X)(X) (IV).

Each X in formula (IV) independently can be any monoanionic ligand disclosed herein, as with each X in formula (I). Thus, each X in formula (IV) independently can be a halide or a $C_1$ to $C_{18}$ hydrocarbyl group in some aspects, while in other aspects, each X independently can be a halide. Moreover, each X independently can be Cl, Br, I, or acetate; alternatively, Br or I; alternatively, acetate; or alternatively, Cl (i.e., the zinc transfer compound having formula (IV) can be ZnCl$_2$).

The reaction solvent can be any suitable solvent, such as an ether solvent or a hydrocarbon solvent. In one aspect, the reaction solvent can comprise a $C_4$ to $C_{20}$ ether; alternatively, a $C_4$ to $C_{10}$ ether; or alternatively, a $C_4$ to $C_8$ ether. In another aspect, the reaction solvent can comprise diethyl ether, diisopropyl ether, di-n-propyl ether, di-n-butyl ether, diphenyl ether, methyl ethyl ether, methyl t-butyl ether, dihydrofuran, tetrahydrofuran (THF), 1,2-dimethoxyethane, 1,4-dioxane, and the like, or any combination of more than one of these materials; alternatively, diethyl ether, THF, 1,4-dioxane, or any combination thereof; alternatively, THF; or alternatively, 1,4-dioxane. In yet another aspect, the reaction solvent can comprise an aliphatic hydrocarbon, an aromatic hydrocarbon, or mixtures or combinations thereof. In still another aspect, the reaction solvent can comprise pentane, hexane, heptane, octane, cyclopentane, cyclohexane, methyl cyclopentane, methyl cyclohexane, benzene, toluene, xylene (including ortho-xylene, meta-xylene, para-xylene, or mixtures thereof), ethylbenzene, or combinations thereof.

In some aspects of this invention, the compound having formula (III) can be the limiting reactant in step (i). In alternative aspects, the zinc metal, zinc-containing transfer agent, or halogen transfer agent and zinc transfer compound can be the limiting reactant in step (i). When a limiting reactant is used in a step of any method disclosed herein, it is meant to infer that substantially all (i.e., at least 85%) of the limiting reactant reacts or is consumed in that step of the method. In some aspects, at least 88%, at least 90%, at least 92%, at least 95%, or at least 98% of the limiting reactant is consumed. An illustrative and non-limiting example of a phenol compound having formula (III) is the following compound (Me=methyl, $^tBu$=tert-butyl):

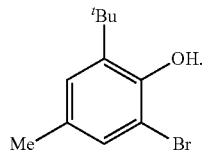

Other illustrative and non-limiting examples of suitable phenol compounds having formula (III) include the following (Me=methyl, $^tBu$=tert-butyl, Et=ethyl, Ad=adamantyl):

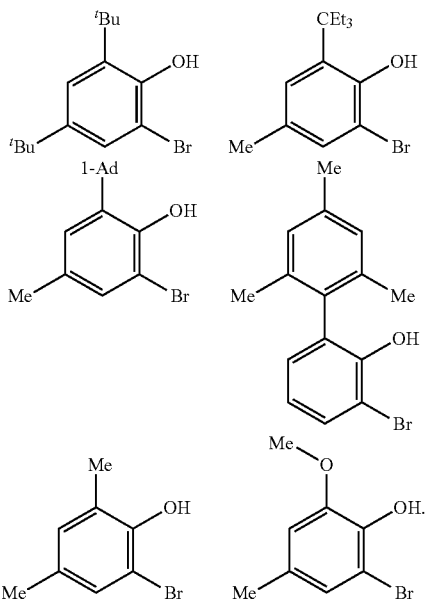

In step (ii), the first mixture of step (i) can be contacted with a palladium cross-coupling catalyst system and the heterocyclic compound having formula (V) to form a ligand reaction mixture comprising the bis(phenol) ligand compound having formula (II). Any suitable palladium cross-coupling catalyst system can be used. For instance, the catalyst system can contain one of more of the following representative and non-limiting palladium catalyst materials: Pd(OAc)$_2$, PdCl$_2$, Pd$_2$(dba)$_3$, Pd(dba)$_2$, Pd(PPh$_3$)$_4$, Pd/C, (MeCN)$_2$PdCl$_2$, and the like, or combinations thereof (Ac=acetate, dba=dibenzylideneactone, Ph=phenyl, and Me=methyl). Often, Pd(OAc)$_2$, Pd$_2$(dba)$_3$, Pd(dba)$_2$, or Pd(PPh$_3$)$_4$, or optionally a mixture or combination thereof, can be used in the palladium cross-coupling catalyst system. In one aspect, the first mixture can be contacted with the palladium cross-coupling catalyst system before the heterocyclic compound having formula (V), while in another aspect, the first mixture can be contacted with the palladium cross-coupling catalyst system after the heterocyclic compound having formula (V), and in yet another aspect, the first mixture can be contacted concurrently with the palladium cross-coupling catalyst system and the heterocyclic compound having formula (V). In some aspects of this invention, the heterocyclic compound having formula (V) can be the limiting reactant in step (ii). Illustrative and non-limiting examples of heterocyclic compounds having formula (V) include the following:

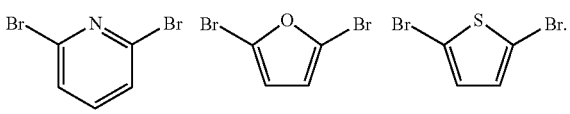

In these and other aspects, the palladium cross-coupling catalyst system can further comprise any suitable phosphorus or N-heterocyclic carbene (NHC) compound (or a mixture thereof), typically at a molar ratio of Pd:P or Pd:NHC in a range from about 5:1 to about 1:5, from about 4:1 to 1:4, from about 3:1 to about 1:3, from about 2:1 to about 1:2, from about 1.5:1 to about 1:1.5, or from about 1.1:1 to about 1:1.1. In an aspect, the phosphorus compound can be a mono, bi, tri, or a tetraphosphorus compound. Additionally or alternatively, the phosphorus compound can have one or more donor atoms selected from N, O, S, or combinations thereof. In some aspects, the phosphorus compound can be a monophosphorus compound of the formula PR$_3$, wherein each R independently can be H, any C$_1$ to C$_{18}$ hydrocarbyl group, halogenated hydrocarbyl group, hydrocarboxy group, or hydrocarbylaminyl group disclosed herein, or any sulfur-containing hydrocarbyl group. Illustrative monophosphorus compounds that are suitable for use in the cross-coupling catalyst system can include, but are not limited to, trimethylphosphine, triethylphosphine, tripropylphosphine, triisopropylphosphine, tributylphosphine, tricyclohexylphosphine, trimethyl phosphite, triethyl phosphite, tripropyl phosphite, triisopropyl phosphite, tributyl phosphite and tricyclohexyl phosphite, triphenylphosphine, tri(o-tolyl)phosphine, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, and the like. Combinations of more than one monophosphorus compound also can be used.

In some aspects, the phosphorus compound can be a diphosphorus compound of the formula R$_2$PYPR$_2$, wherein Y and each R independently can be H, any C$_1$ to C$_{18}$ hydrocarbyl group, halogenated hydrocarbyl group, hydrocarboxy group, or hydrocarbylaminyl group disclosed herein, or any sulfur-containing hydrocarbyl group. Illustrative diphosphorus compounds that are suitable for use in the cross-coupling catalyst system can include, but are not limited to, 2,2'-bis(diphenylphosphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(dicyclohexylphosphino)ethane, 1,3-bis(dicyclohexylphosphino)propane, 1,3-bis(diisopropylphosphino)propane, 1,4-bis(diisopropylphosphino)-butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, and the like. Combinations of more than one diphosphorus compound also can be used.

Representative and non-limiting examples of suitable N-heterocyclic carbene (NHC) materials include the following:

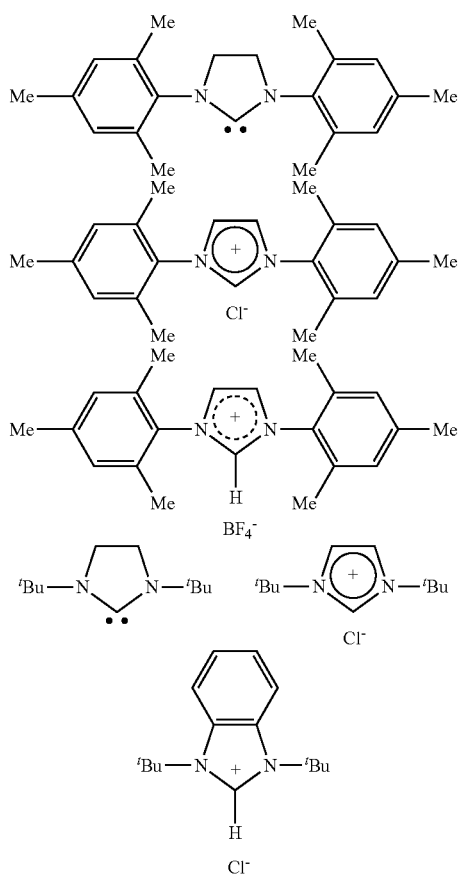

Other suitable NHC materials are described, for example, in U.S. Pat. No. 7,250,510, the disclosure of which is incorporated herein by reference in its entirety.

In aspects of this invention, and optionally, step (ii) can further comprise a purification step, such as extraction and/or crystallization, for example, to isolate/purify/recover the ligand compound having formula (II). Alternatively, and optionally, step (ii) can further comprise a purification step, such as extraction and/or column chromatography, for example, to isolate/purify/recover the ligand compound having formula (II). Moreover, steps (i) and (ii) of the described methods, advantageously, can be conducted in the same vessel. That is, the method of making the bis(phenol) ligand can be a one-pot synthesis.

In step (iii), the ligand compound having formula (II) can be contacted with M(X)(X)(X)(X), optionally in the presence of a second solvent, to form a transition metal compound reaction mixture comprising the transition metal bis(phenol) compound having formula (I). The second solvent can be the same as or different from the reaction solvent, and can comprise any hydrocarbon solvent (e.g., hexane, heptane, cylcohexane, benzene, toluene, xylene, etc.) or any ether solvent (e.g., diethyl ether, THF, 1,4-dioxane, etc.) disclosed herein, as well as combinations thereof. In the compound, M(X)(X)(X)(X), the selections for M and each X are described herein. For instance, M can be Zr or Hf, and each X independently can be a halide or a $C_1$ to $C_{18}$ hydrocarbyl group. As above, one of skill in the art would readily recognize that the two independent monoanionic ligands (X's) in formula (I) can be the same as at least two of the monoanionic ligands in M(X)(X)(X)(X). In some aspects of this invention, the compound, M(X)(X)(X)(X), can be the limiting reactant in step (iii).

Independently, steps (i), (ii), and (iii) of the method of making a transition metal bis(phenolate) compound having formula (I) can be conducted at a variety of temperatures. The temperature at which the respective contacting steps are initiated can be the same as, or different from, the temperature at which the respective contacting steps are allowed to proceed or run for their duration. As an illustrative example, in step (i), the compound having formula (III) and the halogen transfer agent and zinc transfer compound (or zinc metal, or zinc-containing transfer agent) can be combined initially at temperature T1 and, after combining, the temperature can be increased to a temperature T2 for a remainder of the contacting or reacting step to form the first mixture. In an aspect of this invention, the initial contacting in step (i) can be performed at a temperature of less than or equal to about 0° C.; additionally or alternatively, at a temperature greater than or equal to about −100° C.; alternatively, at a temperature in a range from about −85° C. to about 25° C.; or alternatively, at a temperature in a range from about −80° C. to about −30° C. In these and other aspects, after the initial combining, the temperature can be changed to another temperature—for instance, to room temperature in the 20° C. to 25° C. range—for the remainder of the duration of step (i) to form the first mixture.

The appropriate contact or reaction time for each step in the method of making the compound having formula (I) can depend greatly upon the temperature and the reactant concentrations that are selected, among other variables. The initial combining time can be rapid (e.g., less than 5 minutes, less than 1 minute, or less than 30 seconds), but often, the initial combining of components in a particular step may be performed slowly, for example, in a time period ranging from about 15 minutes to about 8 hours; alternatively, from about 30 minutes to about 6 hours; or alternatively, from about 1 hour to about 4 hours. In general, the total contact or reaction time for a particular step in the method can be greater than about 2 minutes, but less than about 1 month. Often, the total time can be from about 5 minutes to about 1 week, from about 30 minutes to about 72 hours, from about 1 hour to about 48 hours, from about 1 hour to about 24 hours, or from about 2 hours to about 12 hours.

This invention contemplates a method further comprising a step of isolating the transition metal bis(phenolate) compound having formula (I) from the transition metal compound reaction mixture. The step of isolating can comprise one or more processes selected from extraction, evaporation, washing, decanting, filtering, drying, and the like, including combinations thereof. It is also contemplated that, if desired, a fine purification step (e.g., crystallization, chromatography, etc.) can be conducted to further isolate and/or purify the bis(phenolate) compound having formula (I).

Synthesis of a Bis(Phenol) Ligand Compound

A method of making a bis(phenol) ligand compound having formula (II) also is disclosed herein:

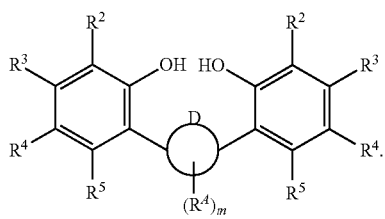
(II)

This method can comprise (i) contacting a phenol compound having the formula:

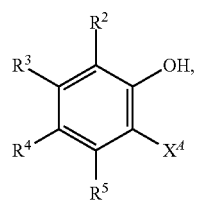
(III)

with
(a) zinc metal;
(b) a zinc-containing transfer agent; or
(c) a halogen transfer agent and a zinc transfer compound;
in the presence of a reaction solvent to form a first mixture; and (ii) contacting the first mixture with a palladium cross-coupling catalyst system and a substituted or unsubstituted, saturated or unsaturated, $C_4$ to $C_8$ heterocyclic compound having the formula:

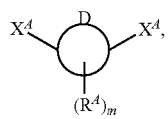
(V)

to form a ligand reaction mixture comprising the bis(phenol) ligand compound having formula (II).

The steps, conditions, and materials in this method for making the ligand compound having formula (II) are the same as those disclosed herein as it relates to the method of making a transition metal bis(phenolate) compound having formula (I), the exception being that step (iii) is not needed to synthesize the ligand compound.

If desired, this method of making the ligand compound can further comprise a step of isolating the ligand compound having formula (II) from the ligand reaction mixture. The step of isolating can comprise one or more processes selected from extraction, evaporation, washing, decanting, filtering, drying, and the like, including combinations thereof. It is also contemplated that, if desired, a fine purification step (e.g., crystallization, chromatography, etc.) can be conducted to further isolate and/or purify the bis(phenol) ligand compound having formula (II).

An illustrative and non-limiting example of a bis(phenol) ligand compound having formula (II) that can be produced using the methods described herein is the following compound (Me=methyl, $^t$Bu=tert-butyl):

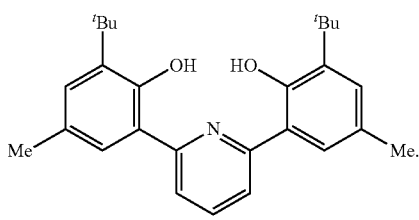 [SMILES: Cc1cc(-c2cccc(-c3cc(C)cc(C(C)(C)C)c3O)n2)c(O)c(C(C)(C)C)c1]

Other illustrative and non-limiting examples of suitable ligand compounds having formula (II) include the following (Me=methyl, $^t$Bu=tert-butyl, Et=ethyl, Ad=adamantyl):

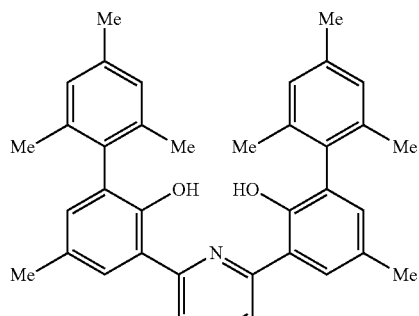

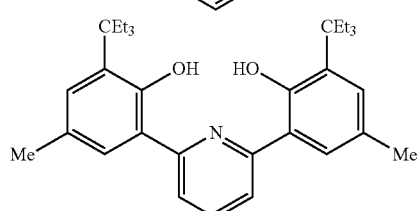

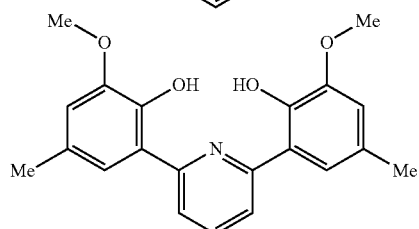

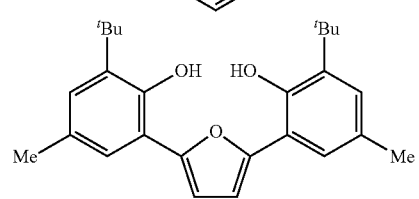

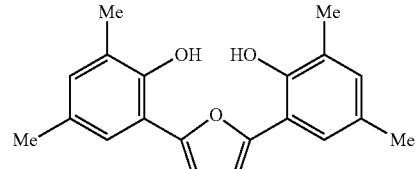

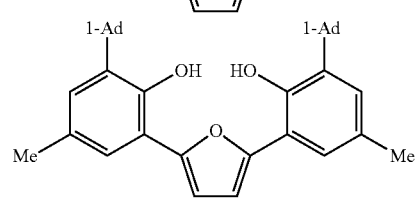

-continued

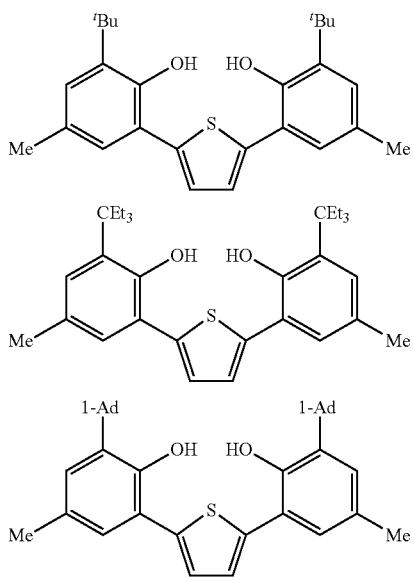

Transition Metal Bis(Phenolate) Compounds

Consistent with aspects of this invention, transition metal bis(phenolate) compounds can have formula (I):

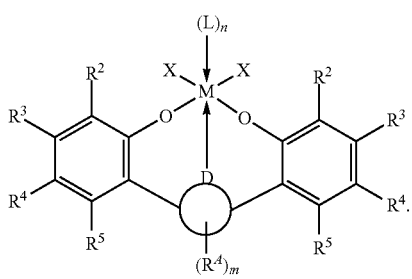

Within formula (I), M, $R^2$, $R^3$, $R^4$, $R^5$, each X, each L, n,

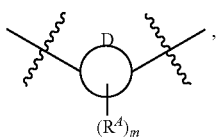

each $R^A$, and m are independent elements of the bis(phenolate) compound. Accordingly, the bis(phenolate) compound having formula (I) can be described using any combination of M, $R^2$, $R^3$, $R^4$, $R^5$, X, L, n,

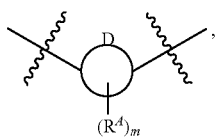

$R^A$, and m disclosed herein. The selections for M, $R^2$, $R^3$, $R^4$, $R^5$, each X, each L, n,

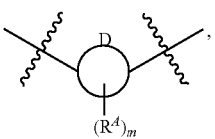

each $R^A$, and m in formula (I) are the same as those described hereinabove for formula (I) as it pertains to the method of making the transition metal bis(phenolate) compound. For instance, $R^2$, $R^3$, $R^4$, and $R^5$ independently can be H or any $C_1$ to $C_{18}$ hydrocarbyl or halogenated hydrocarbyl group disclosed herein (e.g., H or any $C_1$ to $C_6$ alkyl group disclosed herein). Additionally, M can be Ti, Zr, or Hf, and often, M can be Zr or Hf. Each X independently can be any monoanionic ligand disclosed herein (e.g., any halide or $C_1$ to $C_{18}$ hydrocarbyl group disclosed herein), each L independently can be any neutral ligand disclosed herein (e.g., tetrahydrofuran, diethyl ether, acetonitrile, pyridine, dimethyl amine, diethyl amine, trimethyl amine, trimethylphosphine, or triphenylphosphine), and n can be equal to 0, 1 or 2.

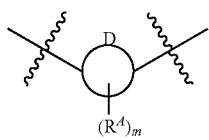

can be any substituted or unsubstituted, saturated or unsaturated, $C_4$ to $C_8$ heterocyclic group disclosed herein, wherein each $R^A$ independently can be any $C_1$ to $C_{18}$ hydrocarbyl or halogenated hydrocarbyl group disclosed herein, and m can be 0, 1, 2, or 3. In some aspects, this heterocyclic group can be:

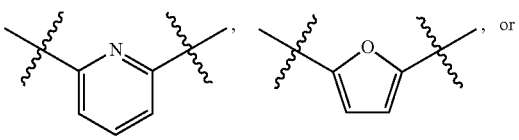

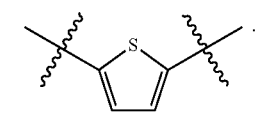

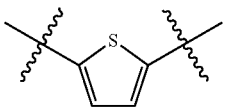

An illustrative and non-limiting example of a transition metal bis(phenolate) compound having formula (I) is the following compound (Me=methyl, $^tBu$=tert-butyl, Bn=benzyl, Et=ethyl):

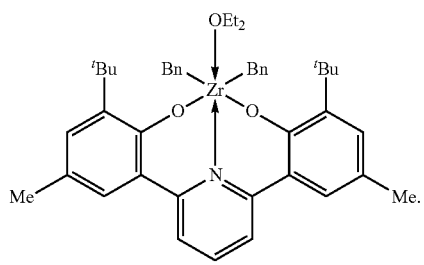

Other illustrative and non-limiting examples of transition metal bis(phenolate) compounds having formula (I) include the following (Me=methyl, $^t$Bu=tert-butyl, Et=ethyl, Bn=benzyl):

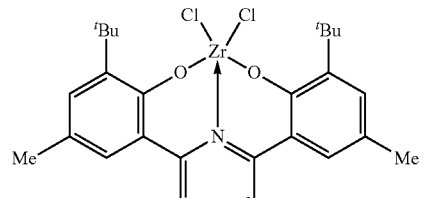

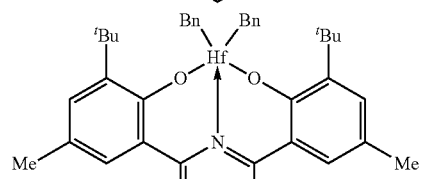

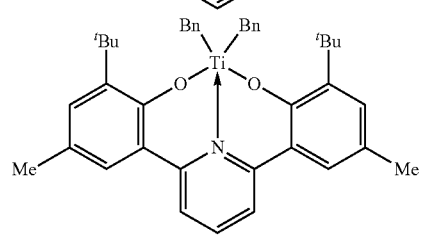

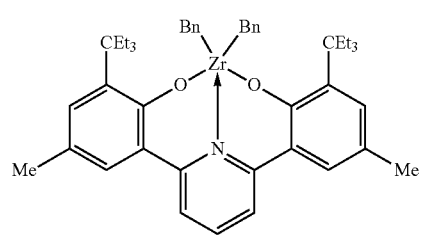

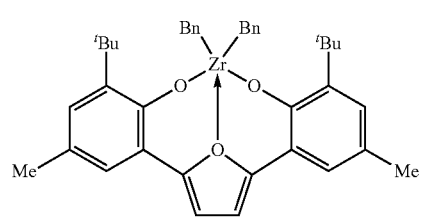

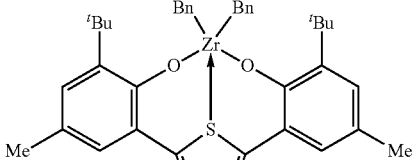

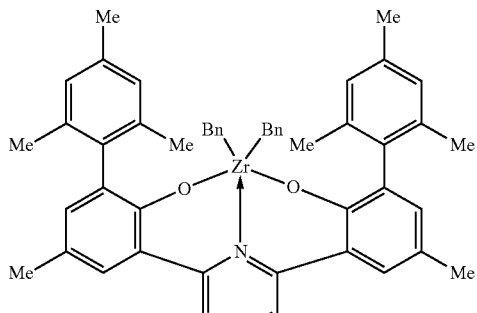

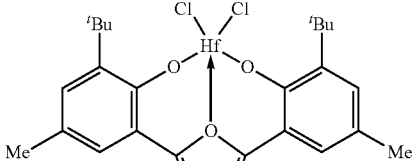

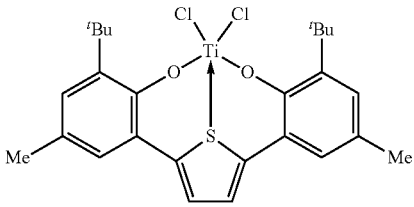

Using analogous synthesis schemes to those provided herein, bis(phenol) ligand and transition metal bis(phenolate) compounds with a heterocyclic group other than a pyridine moiety can be derived, and compounds with $R^2$, $R^3$, $R^4$, and $R^5$ being various hydrocarbyl or halogenated hydrocarbyl substituents can be derived. Moreover, using analogous synthesis schemes to those provided herein, transition metal bis(phenolate) compounds with monoanionic ligands other than Cl or benzyl (e.g., hydrocarbyl, hydrocarbylaminyl, hydrocarbylsilyl, etc.) can be derived, compounds with various transition metals can be derived, and compounds with various neutral ligands can be derived.

Activator-Supports

The present invention encompasses various catalyst compositions containing an activator-support. In one aspect, the activator-support can comprise a solid oxide treated with an electron-withdrawing anion. Alternatively, in another aspect, the activator-support can comprise a solid oxide treated with an electron-withdrawing anion, the solid oxide containing a Lewis-acidic metal ion. Non-limiting examples of suitable activator-supports are disclosed in, for instance, U.S. Pat. Nos. 7,294,599, 7,601,665, 7,884,163, 8,309,485, 8,623,973, and 8,703,886, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form an activator-support, either singly or in combination, can include, but are not limited to, silica-alumina, silica-titania, silica-zirconia, alumina-titania, alumina-zirconia, zinc-aluminate, alumina-boria, silica-boria, aluminophosphate-silica, titania-zirconia, and the like. The solid oxide used herein also can encompass oxide materials such as silica-coated alumina, as described in U.S. Pat. No. 7,884,163.

Accordingly, in one aspect, the solid oxide can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the solid oxide can comprise alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the solid oxide can comprise silica, alumina, titania, zirconia, magnesia, boria, zinc oxide, any mixed oxide thereof, or any combination thereof. In yet another aspect, the solid oxide can comprise silica-alumina, silica-coated alumina, silica-titania, silica-zirconia, alumina-boria, or any combination thereof. In still another aspect, the solid oxide can comprise alumina, silica-alumina, silica-coated alumina, or any mixture thereof; alternatively, alumina; alternatively, silica-alumina; or alternatively, silica-coated alumina.

The silica-alumina or silica-coated alumina solid oxide materials which can be used can have an silica content from about 5 to about 95% by weight. In one aspect, the silica content of these solid oxides can be from about 10 to about 80%, or from about 20% to about 70%, silica by weight. In another aspect, such materials can have silica contents ranging from about 15% to about 60%, or from about 25% to about 50%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, tungstate, molybdate, and the like, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, and the like, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, and the like, or combinations thereof. Yet, in other aspects, the electron-withdrawing anion can comprise fluoride and/or sulfate.

The activator-support generally can contain from about 1 to about 25 wt. % of the electron-withdrawing anion, based on the weight of the activator-support. In particular aspects provided herein, the activator-support can contain from about 1 to about 20 wt. %, from about 2 to about 20 wt. %, from about 3 to about 20 wt. %, from about 2 to about 15 wt. %, from about 3 to about 15 wt. %, from about 3 to about 12 wt. %, or from about 4 to about 10 wt. %, of the electron-withdrawing anion, based on the total weight of the activator-support.

In an aspect, the activator-support can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, as well as any mixture or combination thereof. In another aspect, the activator-support employed in the catalyst systems described herein can be, or can comprise, a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, sulfated silica-coated alumina, and the like, as well as combinations thereof. In yet another aspect, the activator-support can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; or alternatively, fluorided silica-coated alumina. In some aspects, the activator-support can comprise a fluorided solid oxide, while in other aspects, the activator-support can comprise a sulfated solid oxide.

Various processes can be used to form activator-supports useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, and the like, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485, which are incorporated herein by reference in their entirety. Other suitable processes and procedures for preparing activator-supports (e.g., fluorided solid oxides, sulfated solid oxides, etc.) are well known to those of skill in the art.

Co-Catalysts

In certain aspects directed to catalyst compositions containing a co-catalyst, the co-catalyst can comprise a metal hydrocarbyl compound, examples of which include non-halide metal hydrocarbyl compounds, metal hydrocarbyl halide compounds, non-halide metal alkyl compounds, metal alkyl halide compounds, and so forth. The hydrocarbyl group (or alkyl group) can be any hydrocarbyl (or alkyl) group disclosed herein. Moreover, in some aspects, the metal of the metal hydrocarbyl can be a group 1, 2, 11, 12, 13, or 14 metal; alternatively, a group 13 or 14 metal; or alternatively, a group 13 metal. Hence, in some aspects, the metal of the metal hydrocarbyl (non-halide metal hydrocarbyl or metal hydrocarbyl halide) can be lithium, sodium, potassium, rubidium, cesium, beryllium, magnesium, calcium, strontium, barium, zinc, cadmium, boron, aluminum, or tin; alternatively, lithium, sodium, potassium, magnesium, calcium, zinc, boron, aluminum, or tin; alternatively, lithium, sodium, or potassium; alternatively, magnesium or calcium; alternatively, lithium; alternatively, sodium; alternatively, potassium; alternatively, magnesium; alternatively, calcium; alternatively, zinc; alternatively, boron; alternatively, aluminum; or alternatively, tin. In some aspects, the metal hydrocarbyl or metal alkyl, with or without a halide, can comprise a lithium hydrocarbyl or alkyl, a magnesium hydrocarbyl or alkyl, a boron hydrocarbyl or alkyl, a zinc hydrocarbyl or alkyl, or an aluminum hydrocarbyl or alkyl.

In particular aspects directed to catalyst compositions containing a co-catalyst (e.g., the activator can comprise a solid oxide treated with an electron-withdrawing anion), the co-catalyst can comprise an aluminoxane compound, an organoboron or organoborate compound, an ionizing ionic compound, an organoaluminum compound, an organozinc compound, an organomagnesium compound, or an organolithium compound, and this includes any combinations of these materials. In one aspect, the co-catalyst can comprise an organoaluminum compound. In another aspect, the co-catalyst can comprise an aluminoxane compound, an organoboron or organoborate compound, an ionizing ionic compound, an organozinc compound, an organomagnesium compound, an organolithium compound, or any combination thereof. In yet another aspect, the co-catalyst can comprise an aluminoxane compound; alternatively, an organoboron or organoborate compound; alternatively, an ionizing ionic compound; alternatively, an organozinc compound; alternatively, an organomagnesium compound; or alternatively, an organolithium compound.

Specific non-limiting examples of suitable organoaluminum compounds can include trimethylaluminum (TMA), triethylaluminum (TEA), tri-n-propylaluminum (TNPA), tri-n-butylaluminum (TNBA), triisobutylaluminum (TIBA), tri-n-hexylaluminum, tri-n-octylaluminum, diisobutylaluminum hydride, diethylaluminum ethoxide, diethylaluminum chloride, and the like, or combinations thereof. Representative and non-limiting examples of aluminoxanes include methylaluminoxane, modified methylaluminoxane, ethylaluminoxane, n-propylaluminoxane, iso-propylaluminoxane, n-butylaluminoxane, t-butylaluminoxane, sec-butylaluminoxane, iso-butylaluminoxane, 1-pentylaluminoxane, 2-pentylaluminoxane, 3-pentylaluminoxane, isopentylaluminoxane, neopentylaluminoxane, and the like, or any combination thereof. Representative and non-limiting examples of organoboron/organoborate compounds include N,N-dimethylanilinium tetrakis(pentafluorophenyl)borate, triphenylcarbenium tetrakis(pentafluorophenyl)borate, lithium tetrakis(pentafluorophenyl)borate, N,N-dimethylanilinium tetrakis[3,5-bis(trifluoromethyl)phenyl]borate, triphenylcarbenium tetrakis[3,5-bis(trifluoromethyl)phenyl]borate, tris(pentafluorophenyl)boron, tris[3,5-bis(trifluoromethyl)phenyl]boron, and the like, or mixtures thereof.

Examples of ionizing ionic compounds can include, but are not limited to, the following compounds: tri(n-butyl)ammonium tetrakis(p-tolyl)borate, tri(n-butyl) ammonium tetrakis(m-tolyl)borate, tri(n-butyl)ammonium tetrakis(2,4-dimethylphenyl)borate, tri(n-butyl)ammonium tetrakis(3,5-dimethylphenyl)borate, tri(n-butyl)ammonium tetrakis[3,5-bis(trifluoromethyl)phenyl]borate, tri(n-butyl)ammonium tetrakis(pentafluorophenyl)borate, N,N-dimethylanilinium tetrakis(p-tolyl)borate, N,N-dimethylanilinium tetrakis(m-tolyl)borate, N,N-dimethylanilinium tetrakis(2,4-dimethylphenyl)borate, N,N-dimethylanilinium tetrakis(3,5-dimethyl-phenyl)borate, N,N-dimethylanilinium tetrakis[3,5-bis(trifluoromethyl)phenyl]borate, N,N-dimethylanilinium tetrakis(pentafluorophenyl)borate, triphenylcarbenium tetrakis(p-tolyl)borate, triphenylcarbenium tetrakis(m-tolyl)borate, triphenylcarbenium tetrakis(2,4-dimethylphenyl)borate, triphenylcarbenium tetrakis(3,5-dimethylphenyl)borate, triphenylcarbenium tetrakis[3,5-bis(trifluoromethyl)phenyl]borate, triphenylcarbenium tetrakis(pentafluorophenyl)borate, tropylium tetrakis(p-tolyl)borate, tropylium tetrakis(m-tolyl)borate, tropylium tetrakis(2,4-dimethylphenyl)borate, tropylium tetrakis(3,5-dimethylphenyl)borate, tropylium tetrakis[3,5-bis(trifluoromethyl)phenyl]borate, tropylium tetrakis(pentafluorophenyl)borate, lithium tetrakis(pentafluorophenyl)borate, lithium tetraphenylborate, lithium tetrakis(p-tolyl)borate, lithium tetrakis(m-tolyl)borate, lithium tetrakis(2,4-dimethylphenyl)borate, lithium tetrakis(3,5-dimethylphenyl)borate, lithium tetrafluoroborate, sodium tetrakis(pentafluorophenyl)borate, sodium tetraphenylborate, sodium tetrakis(p-tolyl)borate, sodium tetrakis(m-tolyl)borate, sodium tetrakis(2,4-dimethylphenyl)borate, sodium tetrakis(3,5-dimethylphenyl)borate, sodium tetrafluoroborate, potassium tetrakis(pentafluorophenyl)borate, potassium tetraphenylborate, potassium tetrakis(p-tolyl)borate, potassium tetrakis(m-tolyl)borate, potassium tetrakis(2,4-dimethylphenyl)borate, potassium tetrakis(3,5-dimethylphenyl)borate, potassium tetrafluoroborate, lithium tetrakis(pentafluorophenyl)aluminate, lithium tetraphenylaluminate, lithium tetrakis(p-tolyl)aluminate, lithium tetrakis(m-tolyl)aluminate, lithium tetrakis(2,4-dimethylphenyl)aluminate, lithium tetrakis(3,5-dimethylphenyl)aluminate, lithium tetrafluoroaluminate, sodium tetrakis(pentafluorophenyl)aluminate, sodium tetraphenylaluminate, sodium tetrakis(p-tolyl)aluminate, sodium tetrakis(m-tolyl)aluminate, sodium tetrakis(2,4-dimethylphenyl)aluminate, sodium tetrakis(3,5-dimethylphenyl)aluminate, sodium tetrafluoroaluminate, potassium tetrakis(pentafluorophenyl)aluminate, potassium tetraphenylaluminate, potassium tetrakis(p-tolyl)aluminate, potassium tetrakis(m-tolyl)aluminate, potassium tetrakis(2,4-dimethylphenyl)aluminate, potassium tetrakis(3,5-dimethylphenyl)aluminate, potassium tetrafluoroaluminate, and the like, or combinations thereof.

Exemplary organozinc compounds which can be used as co-catalysts can include, but are not limited to, dimethylzinc, diethylzinc, dipropylzinc, dibutylzinc, dineopentylzinc, di(t-rimethylsilyl)zinc, di(triethylsilyl)zinc, di(triisoproplysilyl)zinc, di(triphenylsilyl)zinc, di(allyldimethylsilyl)zinc, di(trimethylsilylmethyl)zinc, and the like, or combinations thereof.

Similarly, exemplary organomagnesium compounds can include, but are not limited to, dimethylmagnesium, diethylmagnesium, dipropylmagnesium, dibutylmagnesium, dineopentylmagnesium, di(trimethylsilylmethyl)magnesium, methylmagnesium chloride, ethylmagnesium chloride, propylmagnesium chloride, butylmagnesium chloride, neopentylmagnesium chloride, trimethylsilylmethylmagnesium chloride, methylmagnesium bromide, ethylmagnesium bromide, propylmagnesium bromide, butylmagnesium bromide, neopentylmagnesium bromide, trimethylsilylmethylmagnesium bromide, methylmagnesium iodide, ethylmagnesium iodide, propylmagnesium iodide, butylmagnesium iodide, neopentylmagnesium iodide, trimethylsilylmethylmagnesium iodide, methylmagnesium ethoxide, ethylmagnesium ethoxide, propylmagnesium ethoxide, butylmagnesium ethoxide, neopentylmagnesium ethoxide, trimethylsilylmethylmagnesium ethoxide, methylmagnesium propoxide, ethylmagnesium propoxide, propylmagnesium propoxide, butylmagnesium propoxide, neopentylmagnesium propoxide, trimethylsilylmethylmagnesium propoxide, methylmagnesium phenoxide, ethylmagnesium phenoxide, propylmagnesium phenoxide, butylmagnesium phenoxide, neopentylmagnesium phenoxide, trimethylsilylmethylmagnesium phenoxide, and the like, or any combinations thereof.

Likewise, exemplary organolithium compounds can include, but are not limited to, methyllithium, ethyllithium, propyllithium, butyllithium (e.g., t-butyllithium), neopentyllithium, trimethylsilylmethyllithium, phenyllithium, tolyllithium, xylyllithium, benzyllithium, (dimethylphenyl)methyllithium, allyllithium, and the like, or combinations thereof.

Co-catalysts that can be used in the catalyst compositions of this invention are not limited to the co-catalysts described above. Other suitable co-catalysts are well known to those of skill in the art including, for example, those disclosed in U.S. Pat. Nos. 3,242,099, 4,794,096, 4,808,561, 5,576,259, 5,807,938, 5,919,983, 7,294,599 7,601,665, 7,884,163, 8,114,946, and 8,309,485, which are incorporated herein by reference in their entirety.

Olefin Monomers

Unsaturated reactants that can be employed with catalyst compositions and polymerization processes of this invention typically can include olefin compounds having from 2 to 30 carbon atoms per molecule and having at least one olefinic double bond. This invention encompasses homopolymerization processes using a single olefin such as ethylene or propylene, as well as copolymerization, terpolymerization, etc., reactions using an olefin monomer with at least one different olefinic compound. For example, the resultant ethylene copolymers, terpolymers, etc., generally can contain a major amount of ethylene (>50 mole percent) and a minor amount of comonomer (<50 mole percent), though this is not a requirement. Comonomers that can be copolymerized with ethylene often can have from 3 to 20 carbon atoms, or from 3 to 10 carbon atoms, in their molecular chain.

Acyclic, cyclic, polycyclic, terminal ($\alpha$), internal, linear, branched, substituted, unsubstituted, functionalized, and non-functionalized olefins can be employed in this invention. For example, typical unsaturated compounds that can be polymerized with the catalyst compositions of this invention can include, but are not limited to, ethylene, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-hexene, 3-ethyl-1-hexene, 1-heptene, 2-heptene, 3-heptene, the four normal octenes (e.g., 1-octene), the four normal nonenes, the five normal decenes, and the like, or mixtures of two or more of these compounds. Cyclic and bicyclic olefins, including but not limited to, cyclopentene, cyclohexene, norbornylene, norbornadiene, and the like, also can be polymerized as described herein. Styrene can also be employed as a monomer in the present invention. In an aspect, the olefin monomer can comprise a $C_2$-$C_{20}$ olefin; alternatively, a $C_2$-$C_{20}$ alpha-olefin; alternatively, a $C_2$-$C_{10}$ olefin; alternatively, a $C_2$-$C_{10}$ alpha-olefin; alternatively, the olefin monomer can comprise ethylene; or alternatively, the olefin monomer can comprise propylene.

When a copolymer (or alternatively, a terpolymer) is desired, the olefin monomer and the olefin comonomer independently can comprise, for example, a $C_2$-$C_{20}$ alpha-olefin. In some aspects, the olefin monomer can comprise ethylene or propylene, which is copolymerized with at least one comonomer (e.g., a $C_2$-$C_{20}$ alpha-olefin, a $C_3$-$C_{20}$ alpha-olefin, etc.). According to one aspect of this invention, the olefin monomer used in the polymerization process can comprise ethylene. In this aspect, examples of suitable olefin comonomers can include, but are not limited to, propylene, 1-butene, 2-butene, 3-methyl-1-butene, isobutylene, 1-pentene, 2-pentene, 3-methyl-1-pentene, 4-methyl-1-pentene, 1-hexene, 2-hexene, 3-ethyl-1-hexene, 1-heptene, 2-heptene, 3-heptene, 1-octene, 1-decene, styrene, and the like, or combinations thereof. According to another aspect of the present invention, the olefin monomer can comprise ethylene, and the comonomer can comprise a $C_3$-$C_{10}$ alpha-olefin; alternatively, the comonomer can comprise 1-butene, 1-pentene, 1-hexene, 1-octene, 1-decene, styrene, or any combination thereof; alternatively, the comonomer can comprise 1-butene, 1-hexene, 1-octene, or any combination thereof; alternatively, the comonomer can comprise 1-butene; alternatively, the comonomer can comprise 1-hexene; or alternatively, the comonomer can comprise 1-octene.

Generally, the amount of comonomer introduced into a polymerization reactor system to produce a copolymer can be from about 0.01 to about 50 weight percent of the comonomer based on the total weight of the monomer and comonomer. According to another aspect of the present invention, the amount of comonomer introduced into a polymerization reactor system can be from about 0.01 to about 40 weight percent comonomer based on the total weight of the monomer and comonomer. In still another aspect, the amount of comonomer introduced into a polymerization reactor system can be from about 0.1 to about 35 weight percent comonomer based on the total weight of the monomer and comonomer. Yet, in another aspect, the amount of comonomer introduced into a polymerization reactor system can be from about 0.5 to about 20 weight percent comonomer based on the total weight of the monomer and comonomer.

While not intending to be bound by this theory, where branched, substituted, or functionalized olefins are used as reactants, it is believed that a steric hindrance can impede and/or slow the polymerization process. Thus, branched and/or cyclic portion(s) of the olefin removed somewhat from the carbon-carbon double bond would not be expected to hinder the reaction in the way that the same olefin substituents situated more proximate to the carbon-carbon double bond might.

According to one aspect of the present invention, at least one monomer/reactant can be ethylene (or propylene), so the polymerization reaction can be a homopolymerization involving only ethylene (or propylene), or a copolymerization with a different acyclic, cyclic, terminal, internal, linear, branched, substituted, or unsubstituted olefin. In addition, the catalyst compositions of this invention can be used in the polymerization of diolefin compounds including, but not limited to, 1,3-butadiene, isoprene, 1,4-pentadiene, and 1,5-hexadiene.

Catalyst Compositions

In some aspects, the present invention employs catalyst compositions containing a transition metal bis(phenolate) compound and an activator-support (one or more than one). These catalyst compositions can be utilized to produce polyolefins—homopolymers, copolymers, and the like—for a variety of end-use applications. Transition metal compounds are discussed hereinabove. In aspects of the present invention, it is contemplated that the catalyst composition can contain more than one transition metal bis(phenolate) compound. Further, additional catalytic compounds—other than those specified as a transition metal bis(phenolate) compound—can be employed in the catalyst compositions and/or the polymerization processes, provided that the additional catalytic compound does not detract from the advantages disclosed herein. Additionally, more than one activator-support also may be utilized.

Generally, catalyst compositions of the present invention comprise a transition metal bis(phenolate) compound having formula (I) and an activator-support (e.g., a solid oxide treated with an electron-withdrawing anion). Activator-supports useful in the present invention are disclosed herein. Optionally, such catalyst compositions can further comprise one or more than one co-catalyst compound or compounds (suitable co-catalysts, such as organoaluminum compounds, also are discussed herein). Thus, a catalyst composition of this invention can comprise a transition metal bis(phenolate) compound, an activator-support, and an organoaluminum compound. For instance, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof; or alternatively, a fluorided solid oxide and/or a sulfated solid oxide. Additionally, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof. Accordingly, a catalyst composition consistent with aspects of the invention can comprise (or consist essentially of, or consist of) a transition metal bis(phenolate) compound; sulfated alumina (or fluorided silica-alumina, or fluorided silica-coated alumina); and triethylaluminum (or triisobutylaluminum).

In one aspect, a catalyst composition of the present invention can comprise a transition metal bis(phenolate) compound having formula (I), a fluorided solid oxide, and optionally, a co-catalyst, such as an organoaluminum compound. Yet, in another aspect, a catalyst composition of the present invention can comprise a transition metal bis(phenolate) compound having formula (I), a sulfated solid oxide, and optionally, a co-catalyst, such as an organoaluminum compound.

In another aspect of the present invention, a catalyst composition is provided which comprises a transition metal bis(phenolate) compound, an activator-support, and an organoaluminum compound, wherein this catalyst composition is substantially free of aluminoxanes, organoboron or organoborate compounds, ionizing ionic compounds, and/or other similar materials; alternatively, substantially free of aluminoxanes; alternatively, substantially free or organoboron or organoborate compounds; or alternatively, substantially free of ionizing ionic compounds. In these aspects, the catalyst composition has catalyst activity, discussed below, in the absence of these additional materials. For example, a catalyst composition of the present invention can consist essentially a transition metal bis(phenolate) compound, an activator-support, and an organoaluminum compound, wherein no other materials are present in the catalyst composition which would increase/decrease the activity of the catalyst composition by more than about 10% from the catalyst activity of the catalyst composition in the absence of said materials.

However, in other aspects of this invention, these activators/co-catalysts can be employed. For example, a catalyst composition comprising a transition metal bis(phenolate) compound and an activator-support can further comprise an optional co-catalyst. Suitable co-catalysts in this aspect can include, but are not limited to, aluminoxane compounds, organoboron or organoborate compounds, ionizing ionic compounds, organoaluminum compounds, organozinc compounds, organomagnesium compounds, organolithium compounds, and the like, or any combination thereof; or alternatively, organoaluminum compounds, organozinc compounds, organomagnesium compounds, organolithium compounds, or any combination thereof. More than one co-catalyst can be present in the catalyst composition.

In a particular aspect contemplated herein, the catalyst composition is a catalyst composition comprising an activator-support (one or more than one) and only one transition metal bis(phenolate) compound having formula (I). In these and other aspects, the catalyst composition can comprise an activator-support comprising a solid oxide treated with an electron-withdrawing anion, only one transition metal bis(phenolate) compound, and a co-catalyst (one or more than one), such as an organoaluminum compound.

This invention further encompasses methods of making these catalyst compositions, such as, for example, contacting the respective catalyst components in any order or sequence. In one aspect, the catalyst composition can be produced by a process comprising contacting the transition metal bis(phenolate) compound and the activator-support, while in another aspect, the catalyst composition can be produced by a process comprising contacting, in any order, the transition metal bis(phenolate) compound, the activator-support, and the co-catalyst.

Generally, the weight ratio of organoaluminum compound to activator-support can be in a range from about 10:1 to about 1:1000. If more than one organoaluminum compound and/or more than one activator-support are employed, this ratio is based on the total weight of each respective component. In another aspect, the weight ratio of the organoaluminum compound to the activator-support can be in a range from about 3:1 to about 1:100, or from about 1:1 to about 1:50.

In some aspects of this invention, the weight ratio of transition metal bis(phenolate) compound to activator-support can be in a range from about 1:1 to about 1:1,000,000. If more than one transition metal bis(phenolate) compound and/or more than activator-support is/are employed, this ratio is based on the total weights of the respective components. In another aspect, this weight ratio can be in a range from about 1:5 to about 1:100,000, or from about 1:10 to about 1:10,000. Yet, in another aspect, the weight ratio of the transition metal bis(phenolate) compound to the activator-support can be in a range from about 1:20 to about 1:1000.

Catalyst compositions of the present invention generally have a catalyst activity greater than about 10 kg of ethylene polymer (homopolymer or copolymer, as the context requires) per gram of the transition metal bis(phenolate) compound per hour (abbreviated kg/g/h). In another aspect, the catalyst activity can be greater than about 20, greater than about 25, or greater than about 30 kg/g/h. In still another aspect, catalyst compositions of this invention can be characterized by having a catalyst activity greater than about 40, greater than about 50, or greater than about 70 kg/g/h, and often can range up to 200-500 kg/g/h. These activities are measured under slurry polymerization conditions, with a triisobutylaluminum co-catalyst, using isobutane as the diluent, at a polymerization temperature of 90° C. and a reactor pressure of about 420 psig. Additionally, in some aspects, the activator-support can comprise sulfated alumina, fluorided silica-alumina, or fluorided silica-coated alumina, although not limited thereto.

Polymerization Processes

Catalyst compositions of the present invention can be used to polymerize olefins to form homopolymers, copolymers, terpolymers, and the like. One such process for polymerizing olefins in the presence of a catalyst composition of the present invention can comprise contacting the catalyst composition with an olefin monomer and optionally an olefin comonomer (one or more) in a polymerization reactor system under polymerization conditions to produce an olefin polymer, wherein the catalyst composition can comprise a transition metal bis (phenolate) compound, an activator-support, and an optional co-catalyst. Suitable transition metal bis(phenolate) compounds, activator-supports, and co-catalysts are discussed herein.

In accordance with one aspect of the invention, the polymerization process can employ a catalyst composition comprising a transition metal bis(phenolate) compound having formula (I) and an activator-support. The catalyst composition, optionally, can further comprise one or more than one organoaluminum compound or compounds (or other suitable co-catalyst). Thus, a process for polymerizing olefins in the presence of a catalyst composition can employ a catalyst composition comprising a transition metal bis(phenolate) compound, an activator-support, and an organoaluminum compound. In some aspects, the activator-support can comprise (or consist essentially of, or consist of) fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, and the like, or combinations thereof; alternatively, a fluorided solid oxide and/or a sulfated solid oxide; alternatively, a fluorided solid oxide; or alternatively, a sulfated solid oxide. In some aspects, the organoaluminum compound can comprise (or consist essentially of, or consist of) trimethylaluminum, triethylaluminum, tri-n-propylaluminum, tri-n-butylaluminum, triisobutylaluminum, tri-n-hexylaluminum, tri-n-octylaluminum, diisobutylaluminum hydride, diethylaluminum ethoxide, diethylaluminum chloride, and the like, or combinations thereof.

In accordance with another aspect of the invention, the polymerization process can employ a catalyst composition comprising a transition metal bis(phenolate) compound, an activator-support, and an optional co-catalyst, wherein the co-catalyst can comprise an aluminoxane compound, an organoboron or organoborate compound, an ionizing ionic compound, an organoaluminum compound, an organozinc compound, an organomagnesium compound, or an organolithium compound, or any combination thereof. Hence, aspects of this invention are directed to a process for polymerizing olefins in the presence of a catalyst composition, the process comprising contacting a catalyst composition with an olefin monomer and optionally an olefin comonomer (one or more) under polymerization conditions to produce an olefin polymer, and the catalyst composition can comprise a transition metal bis(phenolate) compound, an activator-support, and an aluminoxane compound; alternatively, a transition metal bis(phenolate) compound, an activator-support, and an organoboron or organoborate compound; alternatively, a transition metal bis(phenolate) compound, an activator-support, and an ionizing ionic compound; alternatively, a transition metal bis(phenolate) compound, an activator-support, and an organoaluminum compound; alternatively, a transition metal bis(phenolate) compound, an activator-support, and an organozinc compound; alternatively, a transition metal bis (phenolate) compound, an activator-support, and an organomagnesium compound; or alternatively, a transition metal bis(phenolate) compound, an activator-support, and an organolithium compound. Furthermore, more than one co-catalyst can be employed, e.g., an organoaluminum compound and an aluminoxane compound, an organoaluminum compound and an ionizing ionic compound, etc.

In accordance with another aspect of the invention, the polymerization process can employ a catalyst composition comprising only one transition metal bis(phenolate) compound, an activator-support, and an organoaluminum compound.

The catalyst compositions of the present invention are intended for any olefin polymerization method using various types of polymerization reactor systems and reactors. The polymerization reactor system can include any polymerization reactor capable of polymerizing olefin monomers and comonomers (one or more than one comonomer) to produce homopolymers, copolymers, terpolymers, and the like. The various types of reactors include those that can be referred to as a batch reactor, slurry reactor, gas-phase reactor, solution reactor, high pressure reactor, tubular reactor, autoclave reactor, and the like, or combinations thereof. Suitable polymerization conditions are used for the various reactor types. Gas phase reactors can comprise fluidized bed reactors or staged horizontal reactors. Slurry reactors can comprise vertical or horizontal loops. High pressure reactors can comprise autoclave or tubular reactors. Reactor types can include batch or continuous processes. Continuous processes can use intermittent or continuous product discharge. Processes can also include partial or full direct recycle of unreacted monomer, unreacted comonomer, and/or diluent.

Polymerization reactor systems of the present invention can comprise one type of reactor in a system or multiple reactors of the same or different type (e.g., a single reactor, dual reactor, more than two reactors). Production of polymers in multiple reactors can include several stages in at least two separate polymerization reactors interconnected by a transfer device making it possible to transfer the polymers resulting from the first polymerization reactor into the second reactor. The desired polymerization conditions in one of the reactors can be different from the operating conditions of the other reactor(s). Alternatively, polymerization in multiple reactors can include the manual transfer of polymer from one reactor to subsequent reactors for continued polymerization. Multiple reactor systems can include any combination including, but not limited to, multiple loop reactors, multiple gas phase reactors, a combination of loop and gas phase reactors, multiple high pressure reactors, or a combination of high pressure with loop and/or gas phase reactors. The multiple reactors can be operated in series, in parallel, or both. Accordingly, the present invention encompasses polymerization reactor systems comprising a single reactor, comprising two reactors, and comprising more than two reactors. The polymerization reactor system can comprise a slurry reactor, a gas-phase reactor, a solution reactor, in certain aspects of this invention, as well as multi-reactor combinations thereof.

According to one aspect of the invention, the polymerization reactor system can comprise at least one loop slurry reactor comprising vertical or horizontal loops. Monomer, diluent, catalyst, and comonomer can be continuously fed to a loop reactor where polymerization occurs. Generally, continuous processes can comprise the continuous introduction of monomer/comonomer, a catalyst, and a diluent into a polymerization reactor and the continuous removal from this reactor of a suspension comprising polymer particles and the diluent. Reactor effluent can be flashed to remove the solid polymer from the liquids that comprise the diluent, monomer and/or comonomer. Various technologies can be used for this separation step including, but not limited to, flashing that can include any combination of heat addition and pressure reduction, separation by cyclonic action in either a cyclone or hydrocyclone, or separation by centrifugation.

A typical slurry polymerization process (also known as the particle form process) is disclosed, for example, in U.S. Pat. Nos. 3,248,179, 4,501,885, 5,565,175, 5,575,979, 6,239,235, 6,262,191, and 6,833,415, each of which is incorporated herein by reference in its entirety.

Suitable diluents used in slurry polymerization include, but are not limited to, the monomer being polymerized and hydrocarbons that are liquids under polymerization conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another aspect of this invention, the polymerization reactor system can comprise at least one gas phase reactor. Such systems can employ a continuous recycle stream containing one or more monomers continuously cycled through a fluidized bed in the presence of the catalyst under polymerization conditions. A recycle stream can be withdrawn from the fluidized bed and recycled back into the reactor. Simultaneously, polymer product can be withdrawn from the reactor and new or fresh monomer can be added to replace the polymerized monomer. Such gas phase reactors can comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790, and 5,436,304, each of which is incorporated by reference in its entirety herein.

According to still another aspect of the invention, a high pressure polymerization reactor can comprise a tubular reactor or an autoclave reactor. Tubular reactors can have several zones where fresh monomer, initiators, or catalysts are added. Monomer can be entrained in an inert gaseous stream and introduced at one zone of the reactor. Initiators, catalysts, and/or catalyst components can be entrained in a gaseous stream and introduced at another zone of the reactor. The gas streams can be intermixed for polymerization. Heat and pressure can be employed appropriately to obtain optimal polymerization reaction conditions.

According to yet another aspect of the invention, the polymerization reactor system can comprise a solution polymerization reactor wherein the monomer (and comonomer, if used) are contacted with the catalyst composition by suitable stirring or other means. A carrier comprising an inert organic diluent or excess monomer can be employed. If desired, the monomer/comonomer can be brought in the vapor phase into contact with the catalytic reaction product, in the presence or absence of liquid material. The polymerization zone is maintained at temperatures and pressures that will result in the formation of a solution of the polymer in a reaction medium. Agitation can be employed to obtain better temperature control and to maintain uniform polymerization mixtures throughout the polymerization zone. Adequate means are utilized for dissipating the exothermic heat of polymerization.

Polymerization reactor systems suitable for the present invention can further comprise any combination of at least one raw material feed system, at least one feed system for catalyst or catalyst components, and/or at least one polymer recovery system. Suitable reactor systems for the present invention can further comprise systems for feedstock purification, catalyst storage and preparation, extrusion, reactor cooling, polymer recovery, fractionation, recycle, storage, loadout, laboratory analysis, and process control.

Polymerization conditions that are controlled for efficiency and to provide desired polymer properties can include temperature, pressure, and the concentrations of various reactants. Polymerization temperature can affect catalyst productivity, polymer molecular weight, and molecular weight distribution. A suitable polymerization temperature can be any temperature below the de-polymerization temperature according to the Gibbs Free energy equation. Typically, this includes from about 60° C. to about 280° C., for example, or from about 60° C. to about 120° C., depending upon the type of polymerization reactor(s). In some reactor systems, the polymerization temperature generally can fall within a range from about 70° C. to about 100° C., or from about 75° C. to about 95° C. Various polymerization conditions can be held substantially constant, for example, for the production of a particular grade of olefin polymer.

Suitable pressures will also vary according to the reactor and polymerization type. The pressure for liquid phase polymerizations in a loop reactor is typically less than 1000 psig (6.9 MPa). Pressure for gas phase polymerization is usually at about 200 to 500 psig (1.4 MPa to 3.4 MPa). High pressure polymerization in tubular or autoclave reactors is generally run at about 20,000 to 75,000 psig (138 to 517 MPa). Polymerization reactors can also be operated in a supercritical region occurring at generally higher temperatures and pressures. Operation above the critical point of a pressure/temperature diagram (supercritical phase) may offer advantages.

In a particular aspect, and unexpectedly, a polymerization process can comprise contacting a catalyst composition with an olefin monomer and, optionally, an olefin comonomer under polymerization conditions to produce an olefin polymer (e.g., an ethylene homopolymer or copolymer) characterized by a ratio of Mw/Mn in a range from about 1.5 to about 5, and a Mw in a range from about 1,500,000 to about 5,000,000 g/mol. The catalyst composition utilized in this process can comprise a transition metal bis(phenolate) compound, a fluorided solid oxide (e.g., fluorided silica-alumina, fluorided silica-coated alumina, etc.), and an optional co-catalyst.

In another particular aspect, and unexpectedly, a polymerization process can comprise contacting a catalyst composition with an olefin monomer and, optionally, an olefin comonomer under polymerization conditions to produce an olefin polymer (e.g., an ethylene homopolymer or copolymer) characterized by a ratio of Mw/Mn in a range from about 10 to about 200, and a Mw in a range from about 100,000 to about 800,000 g/mol. The catalyst composition utilized in this process can comprise a transition metal bis(phenolate) compound, a sulfated solid oxide (e.g., sulfated silica-alumina, sulfated alumina, etc.), and an optional co-catalyst.

Aspects of this invention also are directed to olefin polymerization processes conducted in the absence of added hydrogen. An olefin polymerization process of this invention can comprise contacting a catalyst composition with an olefin monomer and optionally an olefin comonomer in a polymerization reactor system under polymerization conditions to produce an olefin polymer, wherein the catalyst composition can comprise a transition metal bis(phenolate) compound, an activator, and an optional co-catalyst, and wherein the polymerization process is conducted in the absence of added hydrogen (no hydrogen is added to the polymerization reactor system). As one of ordinary skill in the art would recognize, hydrogen can be generated in-situ by transition metal-based catalyst compositions in various olefin polymerization processes, and the amount generated can vary depending upon the specific catalyst composition and transition metal compound employed, the type of polymerization process used, the polymerization reaction conditions utilized, and so forth.

In other aspects, it may be desirable to conduct the polymerization process in the presence of a certain amount of added hydrogen. Accordingly, an olefin polymerization process of this invention can comprise contacting a catalyst composition with an olefin monomer and optionally an olefin comonomer in a polymerization reactor system under polymerization conditions to produce an olefin polymer, wherein the catalyst composition comprises a transition metal bis (phenolate) compound, an activator, and an optional co-catalyst, and wherein the polymerization process is conducted in the presence of added hydrogen (hydrogen is added to the polymerization reactor system). For example, the ratio of hydrogen to the olefin monomer in the polymerization process can be controlled, often by the feed ratio of hydrogen to the olefin monomer entering the reactor. The added hydrogen to olefin monomer ratio in the process can be controlled at a weight ratio which falls within a range from about 25 ppm to about 1500 ppm, from about 50 to about 1000 ppm, or from about 100 ppm to about 750 ppm.

In some aspects of this invention, the feed or reactant ratio of hydrogen to olefin monomer can be maintained substantially constant during the polymerization run for a particular polymer grade. That is, the hydrogen:olefin monomer ratio can be selected at a particular ratio within a range from about 5 ppm up to about 1000 ppm or so, and maintained at the ratio to within about +/−25% during the polymerization run. For instance, if the target ratio is 100 ppm, then maintaining the hydrogen:olefin monomer ratio substantially constant would entail maintaining the feed ratio between about 75 ppm and about 125 ppm. Further, the addition of comonomer (or comonomers) can be, and generally is, substantially constant throughout the polymerization run for a particular polymer grade.

However, in other aspects, it is contemplated that monomer, comonomer (or comonomers), and/or hydrogen can be periodically pulsed to the reactor, for instance, in a manner similar to that employed in U.S. Pat. No. 5,739,220 and U.S. Patent Publication No. 2004/0059070, the disclosures of which are incorporated herein by reference in their entirety.

The concentration of the reactants entering the polymerization reactor system can be controlled to produce resins with certain physical and mechanical properties. The proposed end-use product that will be formed by the polymer resin and the method of forming that product ultimately can determine the desired polymer properties and attributes. Mechanical properties include tensile, flexural, impact, creep, stress relaxation, and hardness tests. Physical properties include density, molecular weight, molecular weight distribution, melting temperature, glass transition temperature, temperature melt of crystallization, density, stereoregularity, crack growth, long chain branching, and rheological measurements.

This invention is also directed to, and encompasses, the polymers (e.g., ethylene/α-olefin copolymers, ethylene homopolymers, etc.) produced by any of the polymerization processes disclosed herein. Articles of manufacture can be formed from, and/or can comprise, the polymers produced in accordance with this invention.

Polymers and Articles

Olefin polymers encompassed herein can include any polymer produced from any olefin monomer and comonomer(s) described herein. For example, the olefin polymer can comprise an ethylene homopolymer, a propylene homopolymer, an ethylene copolymer (e.g., ethylene/α-olefin, ethylene/1-butene, ethylene/1-hexene, ethylene/1-octene, etc.), a propylene copolymer, an ethylene terpolymer, a propylene terpolymer, and the like, including combinations thereof. In one aspect, the olefin polymer can be an ethylene/1-butene copolymer, an ethylene/1-hexene copolymer, or an ethylene/1-octene copolymer, while in another aspect, the olefin polymer can be an ethylene/1-hexene copolymer.

If the resultant polymer produced in accordance with the present invention is, for example, an ethylene polymer, its properties can be characterized by various analytical techniques known and used in the polyolefin industry. Articles of manufacture can be formed from, and/or can comprise, the ethylene polymers of this invention, whose typical properties are provided below.

The densities of ethylene-based polymers (e.g., ethylene homopolymers, ethylene copolymers) produced using the catalyst systems and processes disclosed herein often are greater than or equal to about 0.89 g/cm$^3$, for example, greater than or equal to about 0.91 g/cm$^3$, or greater than or equal to about 0.92 g/cm$^3$. Yet, in particular aspects, the density can be in a range from about 0.89 to about 0.97, such as, for example, from about 0.91 to about 0.97, from about 0.91 to about 0.965, from about 0.91 to about 0.94, from about 0.92 to about 0.94, or from about 0.925 to about 0.945 g/cm$^3$.

In some aspects, ethylene polymers described herein can have a ratio of Mw/Mn, or the polydispersity index, in a range from about 1.5 to about 5, from about 2 to about 5, from about 1.5 to about 4, from about 2 to about 4, from about 2 to about 3.5, or from about 2.1 to about 3.1. Additionally, the Mw can be in a range from about 1,500,000 to about 5,000,000 g/mol, such as, for example, from about 2,000,000 to about 5,000,000, from about 2,000,000 to about 4,000,000, from about 2,000,000 to about 3,500,000, or from about 2,000,000 to about 3,000,000 g/mol.

In other aspects, ethylene polymers described herein can have a ratio of Mw/Mn, or the polydispersity index, in a range from about 10 to about 200, from about 25 to about 150, from about 25 to about 125, from about 35 to about 175, from about 50 to about 150, from about 65 to about 135, from about 75 to about 175, from about 75 to about 125, or from about 80 to about 140. Additionally, the Mw can be in a range from about 100,000 to about 800,000 g/mol, such as, for example, from about 150,000 to about 750,000, from about 200,000 to about 700,000, from about 250,000 to about 650,000, from about 400,000 to about 800,000, from about 350,000 to about 750,000, from about 350,000 to about 700,000, or from about 400,000 to about 650,000 g/mol.

Olefin polymers, whether homopolymers, copolymers, and so forth, can be formed into various articles of manufacture. Articles which can comprise polymers of this invention include, but are not limited to, an agricultural film, an automobile part, a bottle, a container for chemicals, a drum, a fiber or fabric, a food packaging film or container, a food service article, a fuel tank, a geomembrane, a household container, a liner, a molded product, a medical device or material, an outdoor storage product, outdoor play equipment, a pipe, a sheet or tape, a toy, or a traffic barrier, and the like. Various processes can be employed to form these articles. Non-limiting examples of these processes include injection molding, blow molding, rotational molding, film extrusion, sheet extrusion, profile extrusion, thermoforming, and the like. Additionally, additives and modifiers are often added to these polymers in order to provide beneficial polymer processing or end-use product attributes. Such processes and materials are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety. In some aspects of this invention, an article of manufacture can comprise any of ethylene polymers described herein, and the article of manufacture can be a film product or a molded product.

Applicants also contemplate a method for forming or preparing an article of manufacture comprising a polymer produced by any of the polymerization processes disclosed herein. For instance, a method can comprise (i) contacting a catalyst composition with an olefin monomer and an optional olefin comonomer under polymerization conditions in a polymerization reactor system to produce an olefin polymer, wherein the catalyst composition can comprise a transition metal bis(phenolate) compound, an activator-support comprising a solid oxide treated with an electron-withdrawing anion, and an optional co-catalyst (e.g., an organoaluminum compound); and (ii) forming an article of manufacture comprising the olefin polymer. The forming step can comprise blending, melt processing, extruding, molding, or thermoforming, and the like, including combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Polymer density was determined in grams per cubic centimeter (g/cm$^3$) on a compression molded sample, cooled at about 15° C. per hour, and conditioned for about 40 hours at room temperature in accordance with ASTM D1505 and ASTM D4703.

Molecular weights and molecular weight distributions were obtained using a PL-GPC 220 (Polymer Labs, an Agilent Company) system equipped with a IR4 detector (Polymer Char, Spain) and three Styragel HMW-6E GPC columns (Waters, Mass.) running at 145° C. The flow rate of the mobile phase 1,2,4-trichlorobenzene (TCB) containing 0.5 g/L 2,6-di-t-butyl-4-methylphenol (BHT) was set at 1 mL/min, and polymer solution concentrations were in the range of 1.0-1.5 mg/mL, depending on the molecular weight. Sample preparation was conducted at 150° C. for nominally 4 hr with occasional and gentle agitation, before the solutions were transferred to sample vials for injection. An injection volume of about 200 μL was used. The integral calibration method was used to deduce molecular weights and molecular weight distributions using a Chevron Phillips Chemical Company's HDPE polyethylene resin, MARLEX® BHB5003, as the broad standard. The integral table of the broad standard was pre-determined in a separate experiment with SEC-MALS. Mn is the number-average molecular weight, Mw is the weight-average molecular weight, and Mz is the z-average molecular weight.

Fluorided silica-coated alumina activator-supports were prepared as follows. Bohemite was obtained from W.R. Grace & Company under the designation "Alumina A" and having a surface area of about 300 m$^2$/g, a pore volume of about 1.3 mL/g, and an average particle size of about 100 microns. The alumina was first calcined in dry air at about 600° C. for approximately 6 hours, cooled to ambient temperature, and then contacted with tetraethylorthosilicate in isopropanol to equal 25 wt. % SiO$_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina (FSCA) was collected and stored under dry nitrogen, and was used without exposure to the atmosphere.

Sulfated alumina activator-supports were prepared as follows. As above, bohemite was obtained from W.R. Grace & Company under the designation "Alumina A." This material was impregnated to incipient wetness with an aqueous solution of ammonium sulfate to equal about 15% sulfate. This mixture was then placed in a flat pan and allowed to dry under vacuum at approximately 110° C. for about 16 hours. To calcine the resultant powdered mixture, the material was fluidized in a stream of dry air at about 550° C. for about 6 hours. Afterward, the sulfated alumina (SA) was collected and stored under dry nitrogen, and was used without exposure to the atmosphere.

Nuclear Magnetic Resonance (NMR) spectra were obtained on a Varian Mercury Plus 300 NMR spectrometer operating at 300 MHz for $^1$H NMR (CDCl$_3$ solvent, referenced against the peak of residual CHCl$_3$ at 7.27 ppm).

Example 1

Synthesis of a Bis(Phenol) Ligand Compound

The general reaction scheme used to produce a pyridine bis(phenol) ligand compound having formula (II) is shown below:

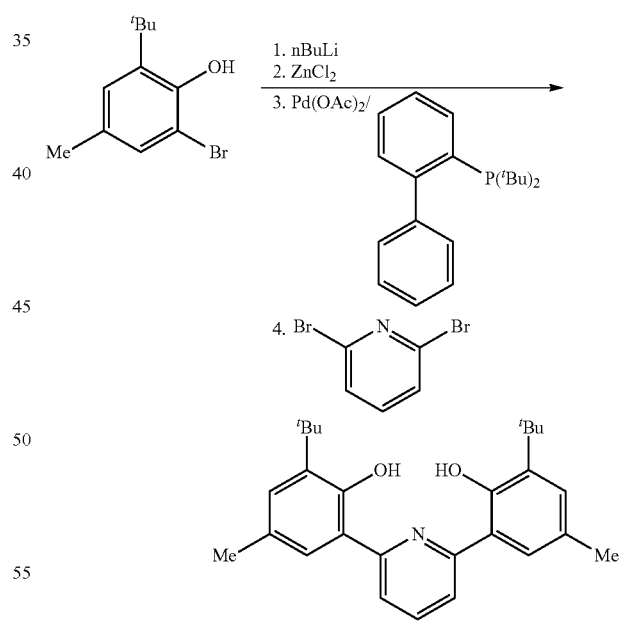

Initially, 2-bromo-4-methyl-6-tert-butylphenol (5.45 g, 22.41 mmol) was charged to a 500-mL round-bottomed flask equipped with a stirbar, and dissolved in 150 mL tetrahydrofuran. After cooling to −78° C., a 2.5 M solution of nBuLi (26.9 mL, 67.24 mmol) in hexanes was added to the flask. This mixture was warmed to ambient temperature and stirred for three hours. Zinc chloride (2.60 g, 19.1 mmol) then was added portionwise to the mixture. This mixture was stirred at ambient temperature until all the zinc chloride was consumed. Next, Pd(OAc)$_2$ (0.194 g, 0.90 mmol) and JohnPhos (0.268 g, 0.90 mmol) were added, followed by 2,6-dibromopyridine (2.38 g, 10.06 mmol). The resultant golden-yellow solution was heated to 70° C., which caused the mixture to darken. This reaction mixture was maintained at 70° C. for 48 hours with stirring. Then, the reaction mixture was quenched with 150 mL of water and 250 mL of diethyl ether. The organics were separated and volatiles were stripped off, leaving a red-brown oil. The oil was extracted with 300 mL of hexanes, concentrated down to 30 mL, and then cooled to −30° C., yielding a yellow solid (1.48 g, 36.5% yield) of the pyridine bis(phenol) ligand compound {$^1$H NMR (CDCl$_3$): δ 10.56 (s, 2H), δ 7.98 (t, 1H), δ 7.64 (d, 2H), δ 7.32 (s, 2H), δ 7.20 (s, 2H), δ 2.37 (s, 6H), δ 1.46 (s, 18H)}.

Example 2

Synthesis of a Transition Metal Bis(Phenolate) Compound

The general reaction scheme used to produce a zirconium bis(phenolate) compound having formula (I) is shown below:

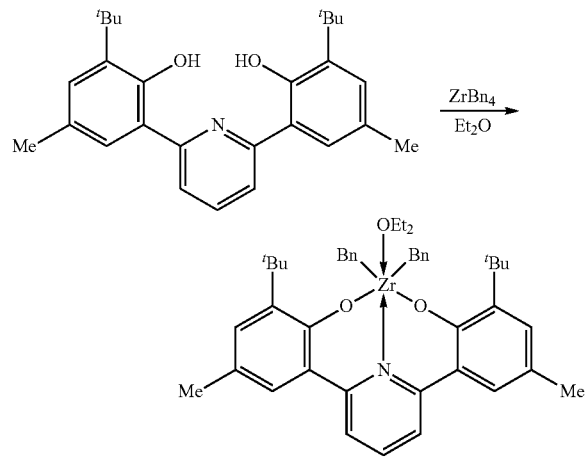

Approximately 30 mL of diethyl ether was added to ZrBn$_4$ (2.44 g, 5.35 mmol, Bn=benzyl), and the mixture was cooled to −30° C. The pyridine bis(phenol) ligand of Example 1 (2.16 g, 5.35 mmol) was dissolved in 20 mL of diethyl ether and added to the cooled solution of diethyl ether and ZrBn$_4$. The resultant yellow suspension was stirred for 4 days. The solid was separated and dried, yielding 3.4 g of the zirconium bis(phenolate) compound {$^1$H NMR (C$_6$D$_6$): δ 7.36 (2H), δ 7.01 (4H), δ 6.94 (2H), δ 6.8 (7H), δ 6.60 (2H), δ 3.28 (4H), δ 2.71 (4H), δ 2.30 (6H), δ 1.77 (18H), δ 1.13 (6H)}. FIG. 1 illustrates the $^1$H-NMR analysis of the zirconium bis(phenolate) compound.

Examples 3-6

Polymers Produced Using a Zirconium Bis(Phenolate) Compound and Activator-supports Examples 3-6 were produced using the following polymerization procedure (Table I summarizes certain information relating to the polymerization experiments of Examples 3-6). The polymerization runs were conducted in a one-gallon stainless steel reactor, and isobutane (1.2 L) was used in all runs. Solutions of the zirconium bis(phenolate) compound were prepared at about 1 mg/mL in toluene. Approximately 0.3-1.0 g of the activator-support (fluorided silica-coated alumina or sulfated alumina), 0.6 mmol of triisobutylaluminum (TIBA), and a solution containing 3 mg of the zirconium bis(phenolate) compound of Example 2 were added in that order through a charge port while slowly venting isobutane vapor. The charge port was closed and isobutane was added. The contents of the reactor were stirred and heated to the desired run temperature of 90 or 95° C., and ethylene was then introduced into the reactor. No hydrogen or 1-hexene was added. Ethylene was fed on demand to maintain the target pressure of 420 psig pressure for the 45 minute length of the polymerization run. The reactor was maintained at the desired temperature throughout the run by an automated heating-cooling system.

As shown in Table I, the catalyst activities for Examples 3-6 were relatively high, ranging from about 70 to about 120 kg of polymer produced per gram of the zirconium bis(phenolate) compound per hour.

Figure 2:
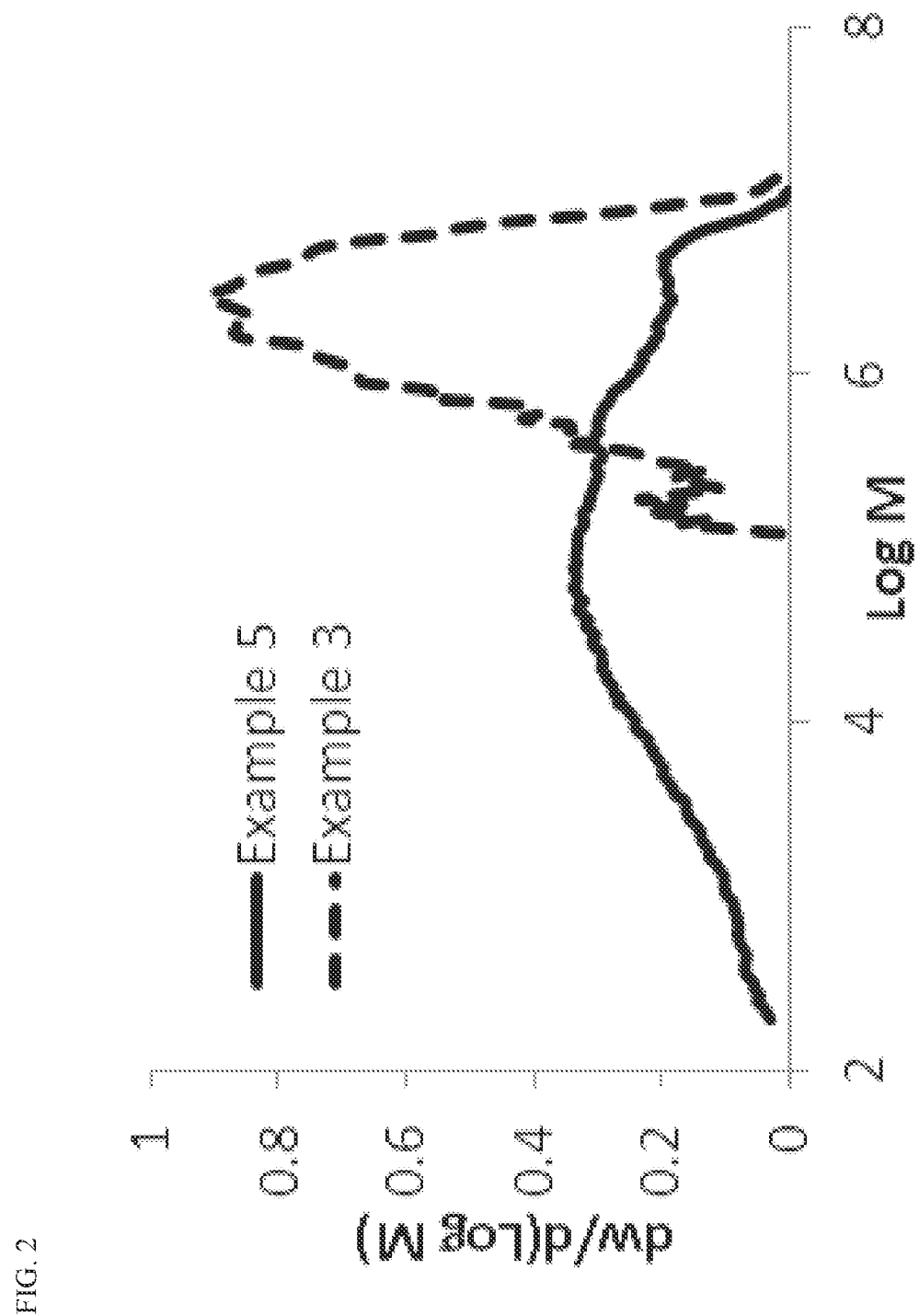
FIG. 2 presents a plot of the molecular weight distributions of the polymers of Example 3 and Example 5.

FIG. 2 illustrates the molecular weight distributions (amount of polymer versus the logarithm of molecular weight) for the polymers of Examples 3 and 5, and Table II summarizes certain density and molecular weight characteristics of the polymers of Examples 3-6. Unexpectedly, the polymers of Examples 3-4, produced using a zirconium bis (phenolate) compound and fluorided silica-coated alumina, had a very high molecular weight (Mw~2,500,000 g/mol), a narrow molecular weight distribution (Mw/Mn~2.5-3.0), and a low density (~0.93-0.94). In contrast, and unexpectedly, the polymers of Examples 5-6, produced using a zirconium bis (phenolate) compound and sulfated alumina, had a molecular weight of ~500,000-550,000 g/mol, a very broad molecular weight distribution (Mw/Mn~90-120), and a high density (~0.96-0.965).

TABLE I

Examples 3-6 - Polymerization Conditions

| Example | Activator-Support | Activator-Support (g) | Temperature (° C.) | Polymer (g) | Activity (kg/g/hr) |
|---------|-------------------|----------------------|--------------------|-------------|--------------------|
| 3 | FSCA | 0.5 | 95 | 235 | 104 |
| 4 | FSCA | 0.3 | 95 | 164 | 73 |
| 5 | SA | 1.0 | 90 | 265 | 118 |
| 6 | SA | 0.5 | 90 | 167 | 74 |

TABLE II

Examples 3-6 - Polymer Characteristics

| Example | Activator-Support | Mw (kg/mol) | Mw/Mn | Density (g/cc) |
|---------|-------------------|-------------|-------|----------------|
| 3 | FSCA | 2571 | 2.6 | 0.9353 |
| 4 | FSCA | 2509 | 2.9 | 0.9337 |
| 5 | SA | 527 | 118.2 | 0.9611 |
| 6 | SA | 525 | 95.0 | 0.9611 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1. A method of making a bis(phenol) ligand compound having the formula:

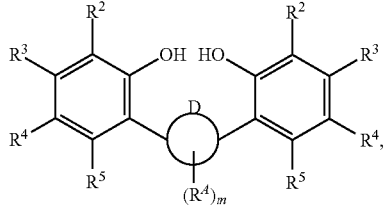
(II)

the method comprising:
(i) contacting a phenol compound having the formula:

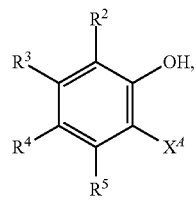
(III)

with
(a) zinc metal;
(b) a zinc-containing transfer agent; or
(c) a halogen transfer agent and a zinc transfer compound;
in the presence of a reaction solvent to form a first mixture; and (ii) contacting the first mixture with a palladium cross-coupling catalyst system and a substituted or unsubstituted, saturated or unsaturated, $C_4$ to $C_8$ heterocyclic compound having the formula:

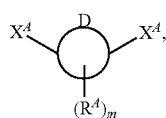
(V)

to form a ligand reaction mixture comprising the bis(phenol) ligand compound having formula (II); wherein:

$R^2$, $R^3$, $R^4$, and $R^5$ independently are H or a $C_1$ to $C_{18}$ hydrocarbyl or halogenated hydrocarbyl group;

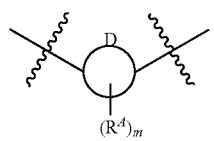

is a substituted or unsubstituted, saturated or unsaturated, $C_4$ to $C_8$ heterocyclic group, wherein each $R^A$ independently is a $C_1$ to $C_{18}$ hydrocarbyl or halogenated hydrocarbyl group, and m is 0, 1, 2, or 3; and each $X^A$ independently is Cl, Br, or I.

Embodiment 2. A method of making a transition metal bis(phenolate) compound having the formula:

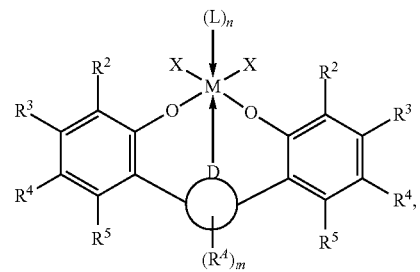
(I)

the method comprising:
(i) contacting a phenol compound having the formula:

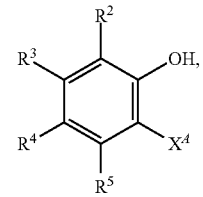
(III)

with
(a) zinc metal;
(b) a zinc-containing transfer agent; or
(c) a halogen transfer agent and a zinc transfer compound;
in the presence of a reaction solvent to form a first mixture;

(ii) contacting the first mixture with a palladium cross-coupling catalyst system and a substituted or unsubstituted, saturated or unsaturated, $C_4$ to $C_8$ heterocyclic compound having the formula:

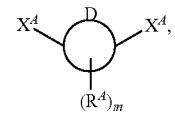
(V)

to form a ligand reaction mixture comprising a bis(phenol) ligand compound having formula (II):

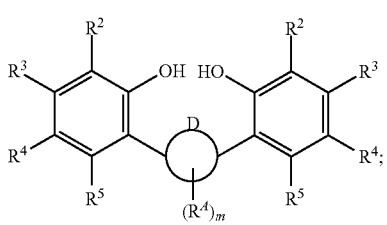
(II)

and
(iii) contacting the ligand compound having formula (II) with M(X)(X)(X)(X), optionally in the presence of a second solvent, to form a transition metal compound reaction mixture comprising the transition metal bis(phenol) compound having formula (I); wherein:

$R^2$, $R^3$, $R^4$, and $R^5$ independently are H or a $C_1$ to $C_{18}$ hydrocarbyl or halogenated hydrocarbyl group;

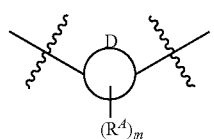

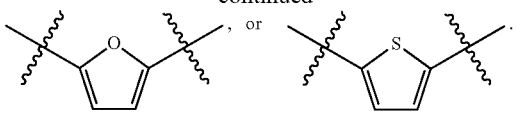

is a substituted or unsubstituted, saturated or unsaturated, $C_4$ to $C_8$ heterocyclic group, wherein each $R^A$ independently is a $C_1$ to $C_{18}$ hydrocarbyl or halogenated hydrocarbyl group, and m is 0, 1, 2, or 3;

each $X^A$ independently is Cl, Br, or I;

M is Ti, Zr, or Hf;

each X independently is a monoanionic ligand; and each L independently is a neutral ligand, wherein n is 0, 1 or 2.

Embodiment 3. The method defined in any one of the preceding embodiments, wherein $R^2$, $R^3$, $R^4$, and $R^5$ independently are H or any $C_1$ to $C_{18}$ hydrocarbyl or halogenated hydrocarbyl group disclosed herein, e.g., a $C_1$ to $C_8$ hydrocarbyl or halogenated hydrocarbyl group, etc.

Embodiment 4. The method defined in any one of the preceding embodiments, wherein $R^2$, $R^3$, $R^4$, and $R^5$ independently are H or any $C_1$ to $C_6$ alkyl group disclosed herein, e.g., methyl, ethyl, propyl, butyl, etc.

Embodiment 5. The method defined in any one of the preceding embodiments, wherein $R^2$ and $R^4$ independently are any $C_1$ to $C_6$ alkyl group disclosed herein, and $R^3$ and $R^5$ are H.

Embodiment 6. The method defined in any one of the preceding embodiments, wherein

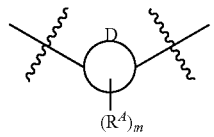

is any heterocyclic group disclosed herein, e.g. a substituted or unsubstituted, saturated or unsaturated, $C_4$ to $C_5$ heterocyclic group, etc., and each $R^A$ independently is any $C_1$ to $C_{18}$ hydrocarbyl or halogenated hydrocarbyl group disclosed herein.

Embodiment 7. The method defined in any one of embodiments 1-6, wherein each $R^A$ independently is a $C_1$ to $C_8$ hydrocarbyl or halogenated hydrocarbyl group.

Embodiment 8. The method defined in any one of embodiments 1-7, wherein m is 0, 1, or 2.

Embodiment 9. The method defined in any one of embodiments 1-8, wherein m is equal to 0.

Embodiment 10. The method defined in any one of embodiments 1-6, wherein

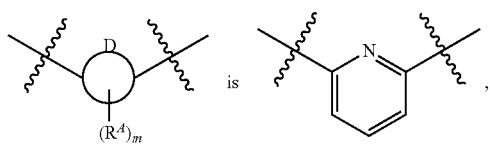

Embodiment 11. The method defined in any one of the preceding embodiments, wherein each $X^A$ independently is Br or I.

Embodiment 12. The method defined in any one of the preceding embodiments, wherein each $X^A$ is Br.

Embodiment 13. The method defined in any one of embodiments 1-12, wherein the phenol compound having the formula (III) is contacted with zinc metal and, optionally, any suitable alkali metal salt and/or alkaline earth metal salt or any alkali metal salt and/or alkaline earth metal salt disclosed herein, e.g., LiCl, NaCl, KCl, NaBr, $MgBr_2$, $MgCl_2$, etc.

Embodiment 14. The method defined in any one of embodiments 1-12, wherein the phenol compound having the formula (III) is contacted with any suitable zinc-containing transfer agent or any zinc-containing transfer agent disclosed herein, e.g., a zinc hydrocarbyl, a zinc alkyl, dimethyl zinc, diethyl zinc, etc.

Embodiment 15. The method defined in embodiment 14, wherein the phenol compound having the formula (III) is contacted with the zinc-containing transfer agent and any suitable alkali metal and/or alkaline earth halogen or alkyl promoter or any alkali metal and/or alkaline earth metal halogen or alkyl promoter disclosed herein, e.g., LiCl, MeLi, NaCl, KCl, NaBr, $MgBr_2$, $MgCl_2$, etc.

Embodiment 16. The method defined in any one of embodiments 1-12, wherein the phenol compound having the formula (III) is contacted with the halogen transfer agent prior to the zinc transfer compound.

Embodiment 17. The method defined in any one of embodiments 1-12 or 16, wherein the halogen transfer agent comprises any suitable strong base, any suitable strong Bronsted base, any alkali metal hydride or hydrocarbon compound disclosed herein, or any alkaline earth metal hydride or hydrocarbon compound disclosed herein.

Embodiment 18. The method defined in any one of embodiments 1-12 or 16, wherein the halogen transfer agent comprises lithium, sodium, potassium or magnesium metal.

Embodiment 19. The method defined in any one of embodiments 1-12 or 16, wherein the halogen transfer agent comprises any hydrocarbyl lithium, sodium, potassium, or magnesium compound disclosed herein, e.g., an alkyl lithium, an alkyl sodium, an alkyl potassium, an alkyl magnesium, an aryl lithium, an aryl sodium, an aryl potassium, an aryl magnesium, etc.

Embodiment 20. The method defined in any one of embodiments 1-12 or 16, wherein the halogen transfer agent comprises MeLi, n-BuLi, t-BuLi, n-hexylLi, $LiCH_2SiMe_3$, $LiCH_2Ph$, $LiCH_2CMe_3$, PrMgCl, PhMgCl, EtMgBr, mesitylmagnesium bromide, $Bu_3MgLi$, $i-PrBu_2MgLi$, or any combination thereof.

Embodiment 21. The method defined in any one of embodiments 1-12 or 16-20, wherein the zinc transfer compound comprises any suitable zinc transfer compound, or any zinc transfer compound disclosed herein.

Embodiment 22. The method defined in any one of embodiments 1-12 or 16-21, wherein the zinc transfer compound has the formula, Zn(X)(X) (IV);

wherein each X in formula (IV) independently is any monoanionic ligand disclosed herein.

Embodiment 23. The method defined in embodiment 22, wherein each X independently is a halide.

Embodiment 24. The method defined in embodiment 22, wherein each X independently Cl, Br, I, or acetate.

Embodiment 25. The method defined in any one of embodiments 1-24, wherein the reaction solvent comprises any suitable hydrocarbon solvent or any hydrocarbon solvent disclosed herein, e.g., benzene, toluene, xylene, hexane, heptane, cyclohexane, etc., as well as combinations thereof.

Embodiment 26. The method defined in any one of embodiments 1-24, wherein the reaction solvent comprises any suitable ether solvent or any ether solvent disclosed herein, e.g., diethyl ether, diisopropyl ether, di-n-propyl ether, di-n-butyl ether, diphenyl ether, methyl ethyl ether, methyl t-butyl ether, dihydrofuran, tetrahydrofuran (THF), 1,2-dimethoxyethane, 1,4-dioxane, etc., as well as combinations thereof.

Embodiment 27. The method defined in any one of the preceding embodiments, wherein the palladium cross-coupling catalyst system comprises any suitable palladium cross-coupling catalyst system, or any palladium cross-coupling catalyst system disclosed herein.

Embodiment 28. The method defined in any one of the preceding embodiments, wherein the palladium cross-coupling catalyst system comprises any suitable palladium material, or any palladium material disclosed herein, e.g., $Pd(OAc)_2$, $PdCl_2$, $Pd_2(dba)_3$, $Pd(dba)_2$, $Pd(PPh_3)_4$, Pd/C, $(MeCN)_2PdCl_2$, etc., or any combination thereof.

Embodiment 29. The method defined in any one of the preceding embodiments, wherein the palladium cross-coupling catalyst system further comprises any suitable phosphorus or N-heterocyclic carbene (NHC) compound or any phosphorus or N-heterocyclic carbene compound disclosed herein, or any combination thereof, at any molar ratio of Pd:P or Pd:NHC disclosed herein, e.g., in a range from about 4:1 to 1:4, from about 1.1:1 to about 1:1.1, etc.

Embodiment 30. The method defined in any one of embodiments 2-29, wherein the second solvent is the same as or different from the reaction solvent, and comprises any hydrocarbon solvent (e.g., toluene, xylene, etc.) or any ether solvent (e.g., diethyl ether, THF, etc.) disclosed herein, as well as combinations thereof.

Embodiment 31. The method defined in any one of embodiments 2-30, wherein M is Zr or Hf.

Embodiment 32. The method defined in any one of embodiments 2-31, wherein each X independently is any suitable monoanionic ligand, or any monoanionic ligand disclosed herein.

Embodiment 33. The method defined in any one of embodiments 2-32, wherein each X independently is H, $BH_4$, a halide, a $C_1$ to $C_{18}$ hydrocarbyl group, a $C_1$ to $C_{18}$ hydrocarboxy group, a $C_1$ to $C_{18}$ hydrocarbylaminyl group, a $C_1$ to $C_{18}$ hydrocarbylsilyl group, a $C_1$ to $C_{18}$ hydrocarbylaminylsilyl group, $OBR^1_2$, or $OSO_2R^1$, wherein $R^1$ is a $C_1$ to $C_{18}$ hydrocarbyl group.

Embodiment 34. The method defined in any one of embodiments 2-33, wherein each X independently is any halide (e.g., Cl) or $C_1$ to $C_{18}$ hydrocarbyl group (e.g., benzyl) disclosed herein.

Embodiment 35. The method defined in any one of embodiments 2-33, wherein each X independently is H, Cl, methyl, phenyl, benzyl, acetylacetonate, or a $C_1$ to $C_8$ alkoxy, aryloxy, alkylamino, dialkylamino, trihydrocarbylsilyl, or hydrocarbylaminosilyl.

Embodiment 36. The method defined in any one of embodiments 2-35, wherein each L independently is any suitable neutral ligand or any neutral ligand disclosed herein, e.g., an ether, an organic carbonyl, a thioether, an amine, a nitrile, a phosphine, etc.

Embodiment 37. The method defined in any one of embodiments 2-36, wherein each L independently is diethyl ether, tetrahydrofuran, acetonitrile, pyridine, dimethyl amine, diethyl amine, trimethyl amine, trimethylphosphine, or triphenylphosphine.

Embodiment 38. The method defined in any one of embodiments 2-37, wherein n is equal to 1.

Embodiment 39. The method defined in any one of embodiments 2-37, wherein n is equal to 0.

Embodiment 40. The method defined in any one of embodiments 1-39, wherein the first mixture is contacted with the palladium cross-coupling catalyst system before the heterocyclic compound having formula (V).

Embodiment 41. The method defined in any one of embodiments 1-39, wherein the first mixture is contacted with the palladium cross-coupling catalyst system after the heterocyclic compound having formula (V).

Embodiment 42. The method defined in any one of embodiments 1-41, wherein the compound having formula (III) is the limiting reactant in step (i).

Embodiment 43. The method defined in any one of embodiments 1-41, wherein the zinc transfer compound is the limiting reactant in step (i).

Embodiment 44. The method defined in any one of embodiments 1-43, wherein the heterocyclic compound having formula (V) is the limiting reactant in step (ii).

Embodiment 45. The method defined in any one of embodiments 2-44, wherein M(X)(X)(X)(X) is the limiting reactant in step (iii).

Embodiment 46. The method defined in any one of embodiments 1-45, wherein the compound having formula (III) and the zinc metal, zinc-containing transfer agent, or halogen transfer agent and zinc transfer compound, are contacted at a temperature in any range disclosed herein, e.g., less than or equal to about 0° C., greater than or equal to about −100° C., etc.

Embodiment 47. The method defined in any one of embodiments 1-46, wherein step (ii) further comprises a purification step comprising extraction and crystallization.

Embodiment 48. The method defined in any one of embodiments 1-46, wherein step (ii) further comprises a purification step comprising extraction and column chromatography.

Embodiment 49. The method defined in any one of embodiments 1-48, wherein steps (i) and (ii) are conducted in the same vessel, e.g., a one-pot synthesis.

Embodiment 50. A catalyst composition comprising any transition metal bis(phenolate) compound disclosed herein, any activator-support disclosed herein, and optionally, any co-catalyst disclosed herein, wherein the transition metal bis(phenolate) compound has the formula:

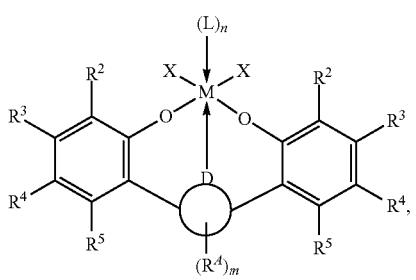

(I)

wherein:

$R^2$, $R^3$, $R^4$, and $R^5$ independently are H or any $C_1$ to $C_{18}$ hydrocarbyl or halogenated hydrocarbyl group disclosed herein (e.g., as defined in any one of embodiments 3-5);

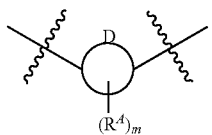

is any substituted or unsubstituted, saturated or unsaturated, $C_4$ to $C_8$ heterocyclic group disclosed herein, wherein each $R^4$ independently is any $C_1$ to $C_{18}$ hydrocarbyl or halogenated hydrocarbyl group disclosed herein, and m is 0, 1, 2, or 3 (e.g., as defined in any one of embodiments 6-10);

M is Ti, Zr, or Hf;

each X independently is any monoanionic ligand disclosed herein (e.g., as defined in any one of embodiments 32-35); and each L independently is any neutral ligand disclosed herein, wherein n is 0, 1 or 2 (e.g., as defined in any one of embodiments 36-39).

Embodiment 51. The composition defined in embodiment 50, wherein the activator-support comprises any solid oxide treated with any electron-withdrawing anion disclosed herein.

Embodiment 52. The composition defined in embodiment 50, wherein the activator-support comprises fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or any combination thereof.

Embodiment 53. The composition defined in embodiment 50, wherein the activator-support comprises a fluorided solid oxide, e.g., fluorided alumina, fluorided silica-alumina, fluorided silica-coated alumina, etc., or any combination thereof.

Embodiment 54. The composition defined in embodiment 50, wherein the activator-support comprises a sulfated solid oxide, e.g., sulfated alumina, sulfated silica-alumina, sulfated silica-coated alumina, etc., or any combination thereof.

Embodiment 55. The composition defined in any one of embodiments 50-54, wherein the activator-support further comprises any metal or metal ion disclosed herein, e.g., zinc, nickel, vanadium, titanium, silver, copper, gallium, tin, tungsten, molybdenum, zirconium, or any combination thereof.

Embodiment 56. The composition defined in any one of embodiments 50-55, wherein the catalyst composition comprises a co-catalyst, e.g., any co-catalyst disclosed herein.

Embodiment 57. The composition defined in any one of embodiments 50-56, wherein the co-catalyst comprises any organoaluminum compound disclosed herein.

Embodiment 58. The composition defined in embodiment 57, wherein the organoaluminum compound comprises trimethylaluminum, triethylaluminum, triisobutylaluminum, or a combination thereof.

Embodiment 59. The composition defined in any one of embodiments 50-58, wherein the catalyst composition is substantially free of aluminoxane compounds, organoboron or organoborate compounds, ionizing ionic compounds, or combinations thereof.

Embodiment 60. The composition defined in any one of embodiments 50-59, wherein the catalyst composition is produced by a process comprising contacting, in any order, the transition metal bis(phenolate) compound having formula (I), the activator-support, and the co-catalyst (if used).

Embodiment 61. The composition defined in any one of embodiments 50-60, wherein a catalyst activity of the catalyst composition is in any range disclosed herein, e.g., from about 20 to about 500, from about 30 to about 300, from about 40 to about 200 kg, etc., of ethylene polymer per gram of transition metal bis(phenolate) compound per hour, under slurry polymerization conditions, with a triisobutylaluminum co-catalyst, using isobutane as a diluent, and with a polymerization temperature of 90° C. and a reactor pressure of 420 psig.

Embodiment 62. An olefin polymerization process, the process comprising contacting the catalyst composition defined in any one of embodiments 50-61 with an olefin monomer and an optional olefin comonomer in a polymerization reactor system under polymerization conditions to produce an olefin polymer.

Embodiment 63. The process defined in embodiment 62, wherein the olefin monomer comprises any olefin monomer disclosed herein, e.g., any $C_2$-$C_{20}$ olefin.

Embodiment 64. The process defined in embodiment 62 or 63, wherein the olefin monomer and the optional olefin comonomer independently comprise a $C_2$-$C_{20}$ alpha-olefin.

Embodiment 65. The process defined in any one of embodiments 62-64, wherein the olefin monomer comprises ethylene.

Embodiment 66. The process defined in any one of embodiments 62-65, wherein the catalyst composition is contacted with ethylene and an olefin comonomer comprising a $C_3$-$C_{10}$ alpha-olefin.

Embodiment 67. The process defined in any one of embodiments 62-66, wherein the catalyst composition is contacted with ethylene and an olefin comonomer comprising 1-butene, 1-hexene, 1-octene, or a mixture thereof.

Embodiment 68. The process defined in any one of embodiments 62-64, wherein the olefin monomer comprises propylene.

Embodiment 69. The process defined in any one of embodiments 62-68, wherein the polymerization reactor system comprises a batch reactor, a slurry reactor, a gas-phase reactor, a solution reactor, a high pressure reactor, a tubular reactor, an autoclave reactor, or a combination thereof.

Embodiment 70. The process defined in any one of embodiments 62-69, wherein the polymerization reactor system comprises a slurry reactor, a gas-phase reactor, a solution reactor, or a combination thereof.

Embodiment 71. The process defined in any one of embodiments 62-70, wherein the polymerization reactor system comprises a loop slurry reactor.

Embodiment 72. The process defined in any one of embodiments 62-71, wherein the polymerization reactor system comprises a single reactor.

Embodiment 73. The process defined in any one of embodiments 62-71, wherein the polymerization reactor system comprises 2 reactors.

Embodiment 74. The process defined in any one of embodiments 62-71, wherein the polymerization reactor system comprises more than 2 reactors.

Embodiment 75. The process defined in any one of embodiments 62-74, wherein the olefin polymer comprises any olefin polymer disclosed herein.

Embodiment 76. The process defined in any one of embodiments 62-67 and 69-75, wherein the olefin polymer is an ethylene homopolymer, an ethylene/1-butene copolymer, an ethylene/1-hexene copolymer, or an ethylene/1-octene copolymer.

Embodiment 77. The process defined in any one of embodiments 62-67 and 69-75, wherein the olefin polymer is an ethylene/1-hexene copolymer.

Embodiment 78. The process defined in any one of embodiments 62-64 and 68-75, wherein the olefin polymer is a polypropylene homopolymer or a propylene-based copolymer.

Embodiment 79. The process defined in any one of embodiments 62-78, wherein the polymerization conditions comprise a polymerization reaction temperature in a range from about 60° C. to about 120° C. and a reaction pressure in a range from about 200 to about 1000 psig (about 1.4 to about 6.9 MPa).

Embodiment 80. The process defined in any one of embodiments 62-79, wherein the polymerization conditions are substantially constant, e.g., for a particular polymer grade.

Embodiment 81. The process defined in any one of embodiments 62-80, wherein no hydrogen is added to the polymerization reactor system.

Embodiment 82. The process defined in any one of embodiments 62-80, wherein hydrogen is added to the polymerization reactor system.

Embodiment 83. The process defined in any one of embodiments 62-82, wherein the olefin polymer has a ratio of Mw/Mn in a range from about 1.5 to about 5, from about 2 to about 4, etc., and a Mw in a range from about 1,500,000 to about 5,000,000 g/mol, from about 2,000,000 to about 3,500,000 g/mol, etc.

Embodiment 84. The process defined in any one of embodiments 62-82, wherein the olefin polymer has a ratio of Mw/Mn in a range from about 10 to about 200, from about 70 to about 150, etc., and a Mw in a range from about 100,000 to about 750,000 g/mol, from about 400,000 to about 800,000 g/mol, etc.

Embodiment 85. The process defined in any one of embodiments 62-84, wherein the olefin polymer has a density in any range disclosed herein, e.g., from about 0.89 to about 0.97, from about 0.91 to about 0.965, from about 0.91 to about 0.94, from about 0.92 to about 0.94 g/cm³, etc.

Embodiment 86. An olefin polymer produced by the polymerization process defined in any one of embodiments 62-85.

Embodiment 87. An article comprising the olefin polymer defined in embodiment 86.

Embodiment 88. A method or forming or preparing an article of manufacture comprising an olefin polymer, the method comprising (i) performing the olefin polymerization process defined in any one of embodiments 62-85 to produce the olefin polymer, and (ii) forming the article of manufacture comprising the olefin polymer, e.g., via any technique disclosed herein.

Embodiment 89. The article defined in embodiment 87 or 88, wherein the article is an agricultural film, an automobile part, a bottle, a drum, a fiber or fabric, a food packaging film or container, a food service article, a fuel tank, a geomembrane, a household container, a liner, a molded product, a medical device or material, a pipe, a sheet or tape, or a toy.

I claim:

1. A method of making a transition metal bis(phenolate) compound having the formula:

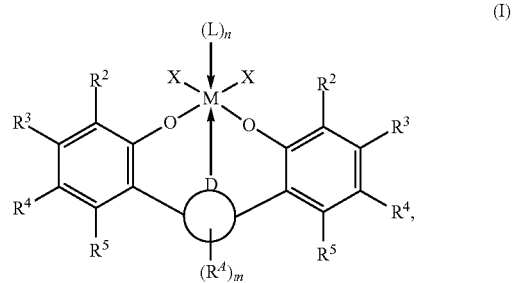

the method comprising:
(i) contacting a phenol compound having the formula:

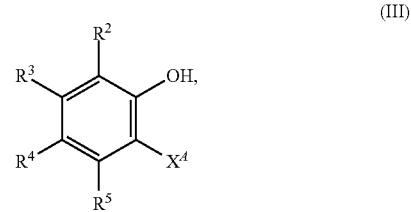

with
(a) zinc metal;
(b) a zinc-containing transfer agent; or
(c) a halogen transfer agent and a zinc transfer compound;
in the presence of a reaction solvent to form a first mixture;
(ii) contacting the first mixture with a palladium cross-coupling catalyst system and a substituted or unsubstituted, saturated or unsaturated, $C_4$ to $C_8$ heterocyclic compound having the formula:

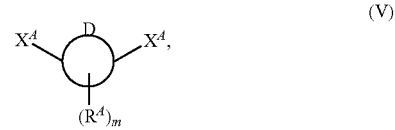

to form a ligand reaction mixture comprising a bis(phenol) ligand compound having formula (II):

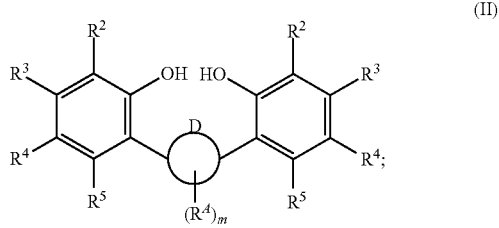

and (iii) contacting the ligand compound having formula (II) with M(X)(X)(X)(X), optionally in the presence of a second solvent, to form a transition metal compound reaction mixture comprising the transition metal bis(phenol) compound having formula (I); wherein:

$R^2$, $R^3$, $R^4$, and $R^5$ independently are H or a $C_1$ to $C_{18}$ hydrocarbyl or halogenated hydrocarbyl group;

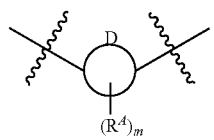

is a substituted or unsubstituted, saturated or unsaturated, $C_4$ to $C_8$ heterocyclic group, wherein each $R^A$ independently is a $C_1$ to $C_{18}$ hydrocarbyl or halogenated hydrocarbyl group, and m is 0, 1, 2, or 3;

each $X^A$ independently is Cl, Br, or I;

M is Ti, Zr, or Hf;

each X independently is a monoanionic ligand; and each L independently is a neutral ligand, wherein n is 0, 1 or 2.

2. The method of claim 1, wherein M is Zr and each X is benzyl.

3. The method of claim 1, wherein each L is independently an ether, an organic carbonyl, a thioether, an amine, a nitrile, or a phosphine.

4. The method of claim 1, wherein each L is independently dimethyl ether, diethyl ether, tetrahydrofuran, furan, benzofuran, tetrahydropyran, 1,4-dioxane, or morpholine.

5. The method of claim 1, wherein L is diethyl ether and n is 1.

6. The method of claim 1, wherein:

$R^2$, $R^3$, $R^4$, and $R^5$ independently are H or a $C_1$ to $C_6$ alkyl group;

each $R^A$ independently is a $C_1$ to $C_8$ hydrocarbyl group;

m is 0, 1, or 2; and each $X^A$ independently is Br or I.

7. The method of claim 6, wherein:

$R^2$ and $R^4$ independently are a $C_1$ to $C_6$ alkyl group, and $R^3$ and $R^5$ are H;

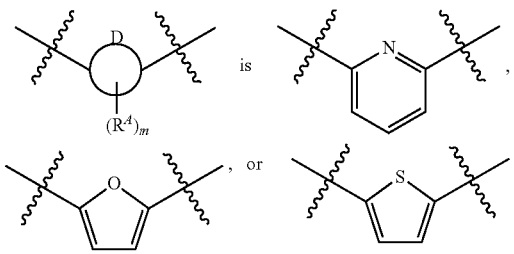

and each $X^A$ is Br.

8. The method of claim 1, wherein the phenol compound having the formula (III) is contacted with zinc metal and an alkali metal salt and/or alkaline earth metal salt.

9. The method of claim 1, wherein the phenol compound having the formula (III) is contacted with the zinc-containing transfer agent.

10. The method of claim 1, wherein the phenol compound having the formula (III) is contacted with:

dimethyl zinc, diethyl zinc, or a combination thereof; and

LiCl, MeLi, NaCl, KCl, NaBr, $MgBr_2$, $MgCl_2$, or a combination thereof.

11.1 The method of claim 1, wherein:

the phenol compound having the formula (III) is contacted with the halogen transfer agent and the zinc transfer compound;

the halogen transfer agent comprises lithium metal, sodium metal, potassium metal, magnesium metal, a hydrocarbyl lithium compound, a hydrocarbyl sodium compound, a hydrocarbyl potassium compound, a hydrocarbyl magnesium compound, or a combination thereof; and the zinc transfer compound has the formula, Zn(X)(X) (IV);

wherein each X in formula (IV) independently is a monoanionic ligand.

12. The method of claim 1, wherein the palladium cross-coupling catalyst system comprises $Pd(OAc)_2$, $PdCl_2$, $Pd_2(dba)_3$, $Pd(dba)_2$, $Pd(PPh_3)_4$, Pd/C, $(MeCN)_2PdCl_2$, or any combination thereof.

13. A method of making a bis(phenol) ligand compound having the formula:

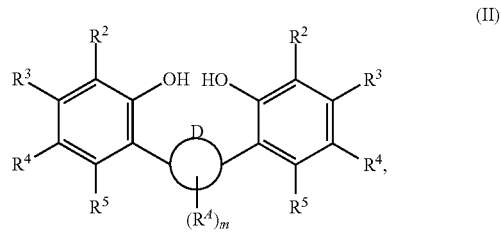

the method comprising:

(i) contacting a phenol compound having the formula:

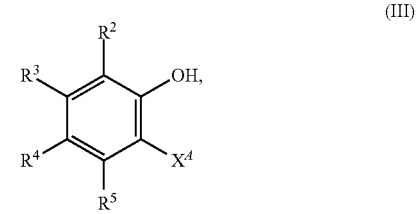

with (a) zinc metal;

(b) a zinc-containing transfer agent; or (c) a halogen transfer agent and a zinc transfer compound; in the presence of a reaction solvent to form a first mixture; and (ii) contacting the first mixture with a palladium cross-coupling catalyst system and a substituted or unsubstituted, saturated or unsaturated, $C_4$ to $C_8$ heterocyclic compound having the formula:

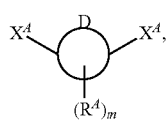

(V)

to form a ligand reaction mixture comprising the bis(phenol) ligand compound having formula (II); wherein:
$R^2$, $R^3$, $R^4$, and $R^5$ independently are H or a $C_1$ to $C_{18}$ hydrocarbyl or halogenated hydrocarbyl group;

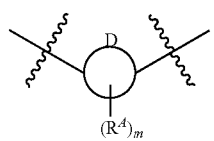

is a substituted or unsubstituted, saturated or unsaturated, $C_4$ to $C_8$ heterocyclic group, wherein each $R^A$ independently is a $C_1$ to $C_{18}$ hydrocarbyl or halogenated hydrocarbyl group, and m is 0, 1, 2, or 3; and
each $X^A$ independently is Cl, Br, or I.

14. The method of claim 13, wherein:
$R^2$, $R^3$, $R^4$, and $R^5$ independently are H or a $C_1$ to $C_6$ alkyl group;
each $R^A$ independently is a $C_1$ to $C_8$ hydrocarbyl group;
m is 0, 1, or 2; and
each $X^A$ independently is Br or I.

15. The method of claim 14, wherein:
$R^2$ and $R^4$ independently are a $C_1$ to $C_6$ alkyl group, and $R^3$ and $R^5$ are H;

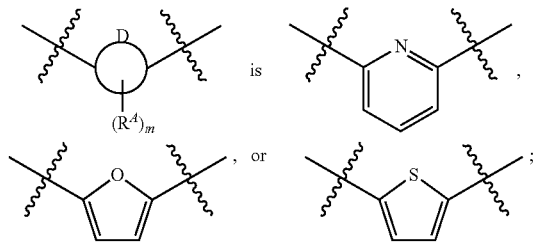

and
each $X^A$ is Br.

16. The method of claim 3, wherein

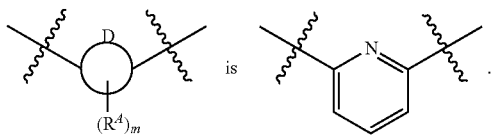

17. The method of claim 13, wherein the phenol compound having the formula (III) is contacted with zinc metal and an alkali metal salt and/or alkaline earth metal salt.

18. The method of claim 13, wherein the phenol compound having the formula (III) is contacted with the zinc-containing transfer agent.

19. The method of claim 13, wherein the phenol compound having the formula (III) is contacted with:
dimethyl zinc, diethyl zinc, or a combination thereof; and
LiCl, MeLi, NaCl, KCl, NaBr, $MgBr_2$, $MgCl_2$, or a combination thereof.

20. The method of claim 13, wherein the phenol compound having the formula (III) is contacted with the halogen transfer agent prior to the zinc transfer compound.

21. The method of claim 13, wherein:
the halogen transfer agent comprises lithium metal, sodium metal, potassium metal, magnesium metal, a hydrocarbyl lithium compound, a hydrocarbyl sodium compound, a hydrocarbyl potassium compound, a hydrocarbyl magnesium compound, or a combination thereof; and
the zinc transfer compound has the formula, $Zn(X)(X)$ (IV);
wherein each X in formula (IV) independently is a monoanionic ligand.

22. The method of claim 13, wherein:
the phenol compound having the formula (III) is contacted with the halogen transfer agent and the zinc transfer compound;
the halogen transfer agent comprises MeLi, n-BuLi, t-BuLi, n-hexylLi, $LiCH_2SiMe_3$, $LiCH_2Ph$, $LiCH_2CMe_3$, PrMgCl, PhMgCl, EtMgBr, mesitylmagnesium bromide, $Bu_3MgLi$, $i-PrBu_2MgLi$, or any combination thereof; and
the zinc transfer compound comprises $ZnCl_2$.

23. The method of claim 13, wherein the reaction solvent comprises an ether solvent.

24. The method of claim 1, wherein:
the phenol compound having the formula (III) is contacted with the halogen transfer agent and the zinc transfer compound;
the halogen transfer agent comprises n-BuLi; and
the zinc transfer compound comprises $ZnCl_2$.

25. The method of claim 13, wherein the palladium cross-coupling catalyst system comprises $Pd(OAc)_2$, $PdCl_2$, $Pd_2(dba)_3$, $Pd(dba)_2$, $Pd(PPh_3)_4$, Pd/C, $(MeCN)_2PdCl_2$, or any combination thereof.

26. The method of claim 25, wherein the palladium cross-coupling catalyst system further comprises a phosphorus compound and/or a N-heterocyclic carbene compound.

* * * * *